US007809511B2

(12) United States Patent
Van Dien et al.

(10) Patent No.: US 7,809,511 B2
(45) Date of Patent: Oct. 5, 2010

(54) METHOD FOR DETERMINING METABOLIC FLUX AFFECTING SUBSTANCE PRODUCTION

(75) Inventors: Stephen Van Dien, Kanagawa (JP); Shintaro Iwatani, Kanagawa (JP); Yoshihiro Usuda, Kanagawa (JP); Kazuhiko Matsui, Kanagawa (JP); Takuji Ueda, Kanagawa (JP); Yuichiro Tsuji, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 1126 days.

(21) Appl. No.: 11/337,580

(22) Filed: Jan. 24, 2006

(65) Prior Publication Data

US 2006/0154289 A1     Jul. 13, 2006

Related U.S. Application Data

(63) Continuation of application No. PCT/JP2004/011212, filed on Jul. 29, 2004.

(30) Foreign Application Priority Data

Jul. 29, 2003   (JP)   ............................ 2003-202842

(51) Int. Cl.
*G06F 19/00*   (2006.01)
(52) U.S. Cl. ....................................................... 702/19
(58) Field of Classification Search ........................ None
See application file for complete search history.

(56) References Cited

U.S. PATENT DOCUMENTS

| 5,175,107 A | 12/1992 | Debabov et al. |
| 6,132,999 A | 10/2000 | Debabov et al. |
| 6,830,903 B1 | 12/2004 | O'Donohue et al. |
| 2002/0142321 A1 | 10/2002 | Palsson et al. |
| 2004/0009578 A1 | 1/2004 | Bathe et al. |

FOREIGN PATENT DOCUMENTS

| WO | WO 00/46405 | 8/2000 |
| WO | WO 02/055995 A2 | 7/2002 |
| WO | WO 02/061115 A2 | 8/2002 |
| WO | WO 02/070730 A2 | 9/2002 |
| WO | WO 03/029425 A2 | 4/2003 |

OTHER PUBLICATIONS

Pinar Calik et al., "Serine alkaline protease overproduction capacity of *Bacillus licheniformis*", Enzyme and Microbial Technology 26 (2000), pp. 45-60.
Amit Varma et al., "Metabolic Flux Balancing: Basic Concepts, Scientific and Practical Use", Bio/Technology vol. 12, Oct. 1994, pp. 994-998.
Steffen Klamt et al., "FluxAnalyzer: exploring structure, pathways, and flux distributions in metabolic networks on interactive flux maps", Bioinformatics vol. 19, No. 2, pp. 261-269, 2003.

Christina Chan et al., "Application of Multivariate Analysis to Optimize Function of Cultured Hepatocytes", Biotechnol. Prog. 2003, 19, pp. 580-598.
Jin-Ho Lee et al., "Global Analysis of Transcriptomes and Proteomes of a Parent Strain and an L-Threonine-Overproducing Mutant Strain", Journal of Bacteriology, vol. 185, No. 18, Sep. 2003, pp. 5442-5451.
Suresh K. Mahajan et al., "Physical Analysis of Spontaneous and Mutagen-Induced Mutants of *Escherichia coli* K-12 Expressing DNA Exonuclease VIII Activity", Genetics 125: 261-273 (Jun. 1990).
Masahiro Iwakura et al., "Studies on Regulatory Functions of Malic Enzymes", J. Biochem, 85, 1355-1365 (1979).
S. H. Hong et al., "Importance of redox balance on the production of succinic acid by metabolically engineered *Escherichia coli*", Appl. Microbiol. Biotechnol. (2002) 58:286-290.
Lucy Stols et al., "Production of Succinic Acid through Overexpression of $NAD^+$-Dependent Mallic Enzyme in an *Escherichia coli* Mutant", Applied and Environmental Microbiology, Jul. 1997, pp. 2695-2701.
Amit Varma et al., "Stoichiometric Flux Balance Models Quantitatively Predict Growth and Metabolic By-Product Secretion in Wild-Type *Escherichia coli* W3110", Applied & Environmental Microbiology, Oct. 1994, pp. 3724-3731.
Christophe H. Schilling et al., "Toward Metabolic Phenomics: Analysis of Genomic Data Using Flux Balances", Biotechnol. Prog., 1999, 15, pp. 288-295.
Christophe H. Schilling et al., "Metabolic Pathway Analysis: Basic Concepts and Scientific Applications in the Post-genomic Era", Biotechol. Prog., 1999, 15, pp. 296-303.
J. Pramanik et al., "Stoichiometric Model of *Escherichia coli* Metabolism: Incorporation of Growth-Rate Dependent Biomass composition and Mechanistic Energy Requirements", Biotechnology & Bioengineering, vol. 56, No. 4, Nov. 20, 1997, pp. 398-421.
Rafael U. Ibarra et al., "*Escherichia coli* K-12 undergoes adaptive evolution to achieve in silito predicted optimal growth", Nature, vol. 420, Nov. 14, 2002, pp. 186-189.
Joseph J. Vallino et al., "Metabolic Flux Distributions in *Corynebacterium glutamicum* During Growth and Lysine Overproduction", Biotechnology & Bioengineering, vol. 41, pp. 633-646 (1993).

(Continued)

*Primary Examiner*—Lori A Clow
(74) *Attorney, Agent, or Firm*—Stephen A. Bent; Foley & Lardner LLP

(57) ABSTRACT

A metabolic flux affecting substance production using cells is determined by 1) creating a stoichiometric matrix based on formulas of biochemical reactions from a substrate through a desired produced substance, 2) selecting the same number of independent metabolic fluxes from all metabolic fluxes as the degree of freedom of the stoichiometric matrix as free fluxes, 3) creating a sufficient number of random combinations of the free fluxes for a statistical analysis and calculating a metabolic flux distribution from each created combination based on the stoichiometric matrix, 4) obtaining a regression equation including a minimum number of free fluxes that shows a correlation with substance production from the calculated metabolic flux distributions by a multivariate statistical analysis, and 5) determining at least one metabolic flux affecting substance production based on a coefficient in the obtained regression equation.

7 Claims, 5 Drawing Sheets

OTHER PUBLICATIONS

Wolfgang Wiechert, "Modeling and simulation: tools for metabolic engineering", Journal of Biotechnology 94, (2002), 37-63.

Wolfgang Wiechert, "Minireview: $^{13}$C Metabolic flux Analysis", Metabolic Engineering 3, 195-206, (2001).

Joanne M. Savinell et al., "Network Analysis of Intermediary Metabolism using Linear Optimization. I. Development of Mathematical Formalism", J. theor. Biol. (1992) 154, pp. 421-454.

Christine Reder, "Metabolic Control Theory: A Structural Approach", J. Theor. Biol., (1988), 135, pp. 175-201.

S.K. Kachigan, "Chapter 4. Regression Analysis in Multivariate Statistical Analysis", $2^{nd}$ Ed., RaDIUS Press, New York, pp. 160-193 (1991).

Notice of Reasons for Rejection Japanese Patent Application No. 2004-221708 dated Jul. 27, 2010.

Noboru Takiguchi et al., "Development of the software to integrate cell and genome information of *Caenorhabditis elegans*", Abstract of the Annual Meeting of the Society for Biotechnology, Japan in Heisei 11 year, 1998, pp. 265 Abstract No. 1151.

SEQUENCE LISTING

<160> NUMBER OF SEQ ID NOS: 35

<210> SEQ ID NO 1
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aatatctttc agttccggca gtaccatacc ttcgcctgaa gcctgctttt ttat          54

<210> SEQ ID NO 2
<211> LENGTH: 54

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agcatggaag aacgccgtaa cttcaacctg ctggggcgct caagttagta taaa            54

<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgacgggcag tcagaagaac caaagttgga gtgcgatgaa gcctgctttt ttat            54

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gacattgaag ttgacgaact cgacccggac aaatttcgct caagttagta taaa            54

<210> SEQ ID NO 5
<211> LENGTH: 120
<212> TYPE: DNA
<213> ORGANISM: Enterobacteria phage lambda

<400> SEQUENCE: 5
agatcttgaa gcctgctttt ttatactaag ttggcattat aaaaaagcat tgcttatcaa     60
tttgttgcaa cgaacaggtc actatcagtc aaaataaaat cattatttga tttcgaattc    120

<210> SEQ ID NO 6
<211> LENGTH: 184
<212> TYPE: DNA
<213> ORGANISM: Enterobacteria phage lambda

<400> SEQUENCE: 6
ctgcagtctg ttacaggtca ctaataccat ctaagtagtt gattcatagt gactgcatat     60
gttgtgtttt acagtattat gtagtctgtt tttatgcaa  aatctaattt aatatattga   120
tatttatatc attttacgtt tctcgttcag ctttttttata ctaacttgag cgtctagaaa   180
gctt                                                                  184

<210> SEQ ID NO 7
<211> LENGTH: 1071
<212> TYPE: DNA
<213> ORGANISM: Enterobacteria phage lambda
<220> FEATURE:
<221> NAME/KEY: CDS
<222> LOCATION: (1)..(1068)

<400> SEQUENCE: 7 atg gga aga agg cga agt cat gag cgc cgg gat tta ccc cct aac ctt      48
Met Gly Arg Arg Arg Ser His Glu Arg Arg Asp Leu Pro Pro Asn Leu
1               5                   10                  15
```

```
tat ata aga aac aat gga tat tac tgc tac agg gac cca agg acg ggt      96
Tyr Ile Arg Asn Asn Gly Tyr Tyr Cys Tyr Arg Asp Pro Arg Thr Gly
         20                  25                  30 aaa gag ttt gga tta ggc aga gac agg cga atc gca atc act gaa gct     144
Lys Glu Phe Gly Leu Gly Arg Asp Arg Arg Ile Ala Ile Thr Glu Ala
     35                  40                  45 ata cag gcc aac att gag tta ttt tca gga cac aaa cac aag cct ctg     192
Ile Gln Ala Asn Ile Glu Leu Phe Ser Gly His Lys His Lys Pro Leu
 50                  55                  60 aca gcg aga atc aac agt gat aat tcc gtt acg tta cat tca tgg ctt     240
Thr Ala Arg Ile Asn Ser Asp Asn Ser Val Thr Leu His Ser Trp Leu
65                  70                  75                  80 gat cgc tac gaa aaa atc ctg gcc agc aga gga atc aag cag aag aca     288
Asp Arg Tyr Glu Lys Ile Leu Ala Ser Arg Gly Ile Lys Gln Lys Thr
                 85                  90                  95 ctc ata aat tac atg agc aaa att aaa gca ata agg agg ggt ctg cct     336
Leu Ile Asn Tyr Met Ser Lys Ile Lys Ala Ile Arg Arg Gly Leu Pro
            100                 105                 110 gat gct cca ctt gaa gac atc acc aca aaa gaa att gcg gca atg ctc     384
Asp Ala Pro Leu Glu Asp Ile Thr Thr Lys Glu Ile Ala Ala Met Leu
        115                 120                 125 aat gga tac ata gac gag ggc aag gcg gcg tca gcc aag tta atc aga     432
Asn Gly Tyr Ile Asp Glu Gly Lys Ala Ala Ser Ala Lys Leu Ile Arg
    130                 135                 140 tca aca ctg agc gat gca ttc cga gag gca ata gct gaa ggc cat ata     480
Ser Thr Leu Ser Asp Ala Phe Arg Glu Ala Ile Ala Glu Gly His Ile
145                 150                 155                 160 aca aca aac cat gtc gct gcc act cgc gca gca aaa tca gag gta agg     528
Thr Thr Asn His Val Ala Ala Thr Arg Ala Ala Lys Ser Glu Val Arg
                165                 170                 175 aga tca aga ctt acg gct gac gaa tac ctg aaa att tat caa gca gca     576
Arg Ser Arg Leu Thr Ala Asp Glu Tyr Leu Lys Ile Tyr Gln Ala Ala
            180                 185                 190 gaa tca tca cca tgt tgg ctc aga ctt gca atg gaa ctg gct gtt gtt     624
Glu Ser Ser Pro Cys Trp Leu Arg Leu Ala Met Glu Leu Ala Val Val
        195                 200                 205 acc ggg caa cga gtt ggt gat tta tgc gaa atg aag tgg tct gat atc     672
Thr Gly Gln Arg Val Gly Asp Leu Cys Glu Met Lys Trp Ser Asp Ile
    210                 215                 220 gta gat gga tat ctt tat gtc gag caa agc aaa aca ggc gta aaa att     720
Val Asp Gly Tyr Leu Tyr Val Glu Gln Ser Lys Thr Gly Val Lys Ile
225                 230                 235                 240 gcc atc cca aca gca ttg cat att gat gct ctc gga ata tca atg aag     768
Ala Ile Pro Thr Ala Leu His Ile Asp Ala Leu Gly Ile Ser Met Lys
                245                 250                 255 gaa aca ctt gat aaa tgc aaa gag att ctt ggc gga gaa acc ata att     816
Glu Thr Leu Asp Lys Cys Lys Glu Ile Leu Gly Gly Glu Thr Ile Ile
            260                 265                 270 gca tct act cgt cgc gaa ccg ctt tca tcc ggc aca gta tca agg tat     864
Ala Ser Thr Arg Arg Glu Pro Leu Ser Ser Gly Thr Val Ser Arg Tyr
        275                 280                 285 ttt atg cgc gca cga aaa gca tca ggt ctt tcc ttc gaa ggg gat ccg     912
Phe Met Arg Ala Arg Lys Ala Ser Gly Leu Ser Phe Glu Gly Asp Pro
    290                 295                 300 cct acc ttt cac gag ttg cgc agt ttg tct gca aga ctc tat gag aag     960
Pro Thr Phe His Glu Leu Arg Ser Leu Ser Ala Arg Leu Tyr Glu Lys
305                 310                 315                 320 cag ata agc gat aag ttt gct caa cat ctt ctc ggg cat aag tcg gac    1008
Gln Ile Ser Asp Lys Phe Ala Gln His Leu Leu Gly His Lys Ser Asp
                325                 330                 335
```

```
acc atg gca tca cag tat cgt gat gac aga ggc agg gag tgg gac aaa    1056
Thr Met Ala Ser Gln Tyr Arg Asp Asp Arg Gly Arg Glu Trp Asp Lys
        340                 345                 350 att gaa atc aaa taa                                                1071
Ile Glu Ile Lys
        355
```

<210> SEQ ID NO 8
<211> LENGTH: 356
<212> TYPE: PRT
<213> ORGANISM: Enterobacteria phage lambda

<400> SEQUENCE: 8

```
Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Glu Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Glu Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
    290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335
```

Thr Met Ala Ser Gln Tyr Arg Asp Asp Arg Gly Arg Glu Trp Asp Lys
        340                 345                 350

Ile Glu Ile Lys
        355

<210> SEQ ID NO 9
<211> LENGTH: 219
<212> TYPE: DNA
<213> ORGANISM: Enterobacteria phage lambda
<220> FEATURE:
<221> NAME/KEY: CDS
<222> LOCATION: (1)..(216)

<400> SEQUENCE: 9 atg tac ttg aca ctt cag gag tgg aac gca cgc cag cga cgt cca aga      48
Met Tyr Leu Thr Leu Gln Glu Trp Asn Ala Arg Gln Arg Arg Pro Arg
1               5                   10                  15 agc ctt gaa aca gtt cgt cga tgg gtt cgg gaa tgc agg ata ttc cca      96
Ser Leu Glu Thr Val Arg Arg Trp Val Arg Glu Cys Arg Ile Phe Pro
            20                  25                  30 cct ccg gtt aag gat gga aga gag tat ctg ttc cac gaa tca gcg gta     144
Pro Pro Val Lys Asp Gly Arg Glu Tyr Leu Phe His Glu Ser Ala Val
        35                  40                  45 aag gtt gac tta aat cga cca gta aca ggt ggc ctt ttg aag agg atc     192
Lys Val Asp Leu Asn Arg Pro Val Thr Gly Gly Leu Leu Lys Arg Ile
    50                  55                  60 aga aat ggg aag aag gcg aag tca tga                                 219
Arg Asn Gly Lys Lys Ala Lys Ser
65                  70

<210> SEQ ID NO 10
<211> LENGTH: 72
<212> TYPE: PRT
<213> ORGANISM: Enterobacteria phage lambda

<400> SEQUENCE: 10

Met Tyr Leu Thr Leu Gln Glu Trp Asn Ala Arg Gln Arg Arg Pro Arg
1               5                   10                  15

Ser Leu Glu Thr Val Arg Arg Trp Val Arg Glu Cys Arg Ile Phe Pro
            20                  25                  30

Pro Pro Val Lys Asp Gly Arg Glu Tyr Leu Phe His Glu Ser Ala Val
        35                  40                  45

Lys Val Asp Leu Asn Arg Pro Val Thr Gly Gly Leu Leu Lys Arg Ile
    50                  55                  60

Arg Asn Gly Lys Lys Ala Lys Ser
65                  70

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctagtaagat cttgaagcct gctttttat actaagttgg                            40

<210> SEQ ID NO 12
<211> LENGTH: 41
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 12
atgatcgaat tcgaaatcaa ataatgattt tattttgact g                           41

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atgccactgc agtctgttac aggtcactaa taccatctaa g                           41

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
accgttaagc tttctagacg ctcaagttag tataaaaaag ctgaac                      46

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ttcttagacg tcaggtggca cttttcgggg aaatgtgc                               38

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
taacagagat ctcgcgcaga aaaaaggat ctcaaga                                 37

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aacagagatc taagcttaga tcctttgcct ggcggcagta gcgcgg                      46

<210> SEQ ID NO 18
<211> LENGTH: 35
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 18
ataaactgca gcaaaaagag tttgtagaaa cgcaa                              35

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agtaattcta gaaagcttaa cacagaaaaa agcccg                             36

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctagtaggat ccctgcagtg gtcgaaaaaa aaagcccgca ctg                     43

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atcgaggtac cagatctccg gataagtaga cagcctg                            37

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaaggtctag agcgcccggt tgacgctgct ag                                 32

<210> SEQ ID NO 23
<211> LENGTH: 1388
<212> TYPE: DNA
<213> ORGANISM: Artificial Sequence
<220> FEATURE:
<223> OTHER INFORMATION: Description of Artificial Sequence: Synthetic
      DNA fragment sequence

<400> SEQUENCE: 23
gaattctcat gtttgacagc ttatcatcga taagctttaa tgcggtagtt tatcacagtt    60
aaattgctaa cgcagtcagg caccgtgtat gaaatctaac aatgcgctca tcgtcatcct   120
cggcaccgtc accctggatg ctgtaggcat aggcttggtt atgccggtac tgccgggcct   180
cttgcgggat atcgtccatt ccgacagcat cgccagtcac tatggcgtgc tgctagcgct   240
atatgcgttg atgcaatttc tatgcgcacc cgttctcgga gcactgtccg accgctttgg   300
```

```
ccgccgccca gtcctgctcg cttcgctact tggagccact atcgactacg cgatcatggc      360
gaccacaccc gtcctgtgga tcctctacgc cggacgcatc gtggccggca tcaccggcgc      420
cacaggtgcg gttgctggcg cctatatcgc cgacatcacc gatggggaag atcgggctcg      480
ccacttcggg ctcatgagcg cttgtttcgg cgtgggtatg gtggcaggcc ccgtggccgg      540
gggactgttg ggcgccatct ccttgcatgc accattcctt cgcggcggcg tgctcaacgg      600
cctcaaccta ctactgggct gcttcctaat gcaggagtcg cataagggag agcgtcgacc      660
gatgcccttg agagccttca acccagtcag ctccttccgg tgggcgcggg gcatgactat      720
cgtcgccgca cttatgactg tcttctttat catgcaactc gtaggacagg tgccggcagc      780
gctctgggtc attttcggcg aggaccgctt tcgctggagc gcgacgatga tcggcctgtc      840
gcttgcggta ttcggaatct tgcacgccct cgctcaagcc ttcgtcactg gtcccgccac      900
caaacgtttc ggcgagaagc aggccattat cgccggcatg gcggccgacg cgctgggcta      960
cgtcttgctg gcgttcgcga cgcgaggctg gatggccttc cccattatga ttcttctcgc     1020
ttccggcggc atcgggatgc ccgcgttgca ggccatgctg tccaggcagg tagatgacga     1080
ccatcaggga cagcttcaag gatcgctcgc ggctcttacc agcctaactt cgatcactgg     1140
accgctgatc gtcacggcga tttatgccgc ctcggcgagc acatggaacg ggttggcatg     1200
gattgtaggc gccgccctat accttgtctg cctccccgcg ttgcgtcgcg gtgcatggag     1260
ccgggccacc tcgacctgaa tggaagccgg cggcacctcg ctaacggatt caccactcca     1320
actagaaagc ttaacacaga aaaaagcccg cacctgacag tgcgggcttt ttttttcgac     1380
cactgcag                                                              1388

<210> SEQ ID NO 24
<211> LENGTH: 1162
<212> TYPE: DNA
<213> ORGANISM: Artificial Sequence
<220> FEATURE:
<223> OTHER INFORMATION: Description of Artificial Sequence: Synthetic
      DNA fragment sequence

<400> SEQUENCE: 24
agatctccgg ataagtagac agcctgataa gtcgcacgaa aaacaggtat tgacaacatg       60
aagtaacatg cagtaagata caaatcgcta ggtaacacta gcagcgtcaa ccgggcgctc      120
tagctagagc caagctagct tggccggatc cgagattttc aggagctaag gaagctaaaa      180
tggagaaaaa aatcactgga tataccaccg ttgatatatc ccaatggcat cgtaaagaac      240
attttgaggc atttcagtca gttgctcaat gtacctataa ccagaccgtt cagctggata      300
ttacggcctt tttaaagacc gtaaagaaaa ataagcacaa gttttatccg gcctttattc      360
acattcttgc ccgcctgatg aatgctcatc cggaattccg tatggcaatg aaagacggtg      420
agctggtgat atgggatagt gttcacccct tgttacaccg ttttccatga gcaaactgaa      480 acgttttcatc gctctggagt gaataccacg acgatttccg gcagtttcta cacatatatt      540
cgcaagatgt ggcgtgttac ggtgaaaacc tggcctattt ccctaaaggg tttattgaga      600
atatgttttt cgtctcagcc aatccctggg tgagtttcac cagttttgat ttaaacgtgg      660
ccaatatgga caacttcttc gcccccgttt tcaccatggg caaatattat acgcaaggcg      720
acaaggtgct gatgccgctg gcgattcagg ttcatcatgc cgtctgtgat ggcttccatg      780
tcggcagaat gcttaatgaa ttacaacagt actgcgatga gtggcagggc ggggcgtaat      840 tttttttaagg cagttattgg tgcccttaaa cgcctggtgc tacgcctgaa taagtgataa      900
```

-continued

```
taagcggatg aatggcagaa attcgtcgaa gcttaacaca gaaaaaagcc cgcacctgac      960
agtgcgggct ttttttttcg accactgcag tctgttacag gtcactaata ccatctaagt     1020
agttgattca tagtgactgc atatgttgtg ttttacagta ttatgtagtc tgttttttat     1080
gcaaaatcta atttaatata ttgatattta tcatttta cgtttctcgt tcagcttttt      1140
tatactaact tgagcgtcta ga                                              1162
```

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

```
ctaatatcga tgaagattct tgctcaa                                           27
```

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

```
gcgttgaatt ccatacaacc tccttagtac atgc                                   34
```

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

```
gtactagaat tcgtgtaatt gcggagactt tgcg                                   34
```

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

```
aatagcctgc agttatttga tttcaatttt gtcccactcc c                           41
```

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
ttcttagacg tcaggtggca cttttcgggg aaatgtgc                               38
```

<210> SEQ ID NO 30
<211> LENGTH: 37

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
taacagagat ctagcgcaga aaaaaaggat ctcaaga                               37

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ataaactgca gcaaaaagag tttgtagaaa cgcaa                                 35

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aacagaagct ttttgcctgg cggcagtagc gcgg                                  34

<210> SEQ ID NO 33
<211> LENGTH: 879
<212> TYPE: DNA
<213> ORGANISM: Artificial Sequence
<220> FEATURE:
<223> OTHER INFORMATION: Description of Artificial Sequence: Synthetic
      DNA fragment sequence

<400> SEQUENCE: 33
tcgatgaaga ttcttgctca attgttatca gctatgcgcc gaccagaaca ccttgccgat      60
cagccaaacg tctcttcagg ccactgacta gcgataactt tccccacaac ggaacaactc     120
tcattgcatg ggatcattgg gtactgtggg tttagtggtt gtaaaaacac ctgaccgcta     180
tccctgatca gtttcttgaa ggtaaactca tcaccccaa gtctggctat cagaaatca      240 cctggctcaa cagcctgctc agggtcaacg agaattaaca ttccgtcagg aaagcttggc     300
ttggagcctg ttggtgcggt catggaatta ccttcaacct caagccagaa tgcagaatca     360
ctggcttttt tggttgtgct tacccatctc tccgcatcac ctttggtaaa ggttctaagc     420
tcaggtgaga acatccctgc ctgaacatga gaaaaaacag ggtactcata ctcacttcta     480
agtgacggct gcatactaac cgcttcatac atctcgtaga tttctctggc gattgaaggg     540
ctaaattctt caacgctaac tttgagaatt tttgcaagca atgcggcgtt ataagcattt     600
aatgcattga tgccattaaa taaagcacca acgcctgact gccccatccc catcttgtct     660
gcgacagatt cctgggataa gccaagttca tttttctttt tttcataaat tgctttaagg     720
cgacgtgcgt cctcaagctg ctcttgtgtt aatggtttct tttttgtgct catacgttaa     780
atctatcacc gcaagggata aatatctaac accgtgcgtg ttgactattt tacctctggc     840
ggtgataatg gttgcatgta ctaaggaggt tgtatggaa                            879

<210> SEQ ID NO 34
```

<211> LENGTH: 1290
<212> TYPE: DNA
<213> ORGANISM: Artificial Sequence
<220> FEATURE:
<223> OTHER INFORMATION: Description of Artificial Sequence: Synthetic
      DNA fragment sequence

<400> SEQUENCE: 34

| | | | | | |
|---|---|---|---|---|---|
| attatttgat | ttcaattttg | tcccactccc | tgcctctgtc | atcacgatac | tgtgatgcca | 60 |
| tggtgtccga | cttatgcccg | agaagatgtt | gagcaaactt | atcgcttatc | tgcttctcat | 120 |
| agagtcttgc | agacaaactg | cgcaactcgt | gaaaggtagg | cggatcccct | tcgaaggaaa | 180 |
| gacctgatgc | ttttcgtgcg | cgcataaaat | accttgatac | tgtgccggat | gaaagcggtt | 240 |
| cgcgacgagt | agatgcaatt | atggtttctc | cgccaagaat | ctctttgcat | ttatcaagtg | 300 |
| tttccttcat | tgatattccg | agagcatcaa | tatgcaatgc | tgttgggatg | gcaattttta | 360 |
| cgcctgtttt | gctttgctcg | acataaagat | atccatctac | gatatcagac | cacttcattt | 420 |
| cgcataaatc | accaactcgt | tgcccggtaa | caacagccag | ttccattgca | agtctgagcc | 480 |
| aacatggtga | tgattctgct | gcttgataaa | ttttcaggta | ttcgtcagcc | gtaagtcttg | 540 |
| atctccttac | ctctgatttt | gctgcgcgag | tggcagcgac | atggtttgtt | gttatatggc | 600 |
| cttcagctat | tgcctctcgg | aatgcatcgc | tcagtgttga | tctgattaac | ttggctgacg | 660 |
| ccgccttgcc | ctcgtctatg | tatccattga | gcattgccgc | aatttctttt | gtggtgatgt | 720 |
| cttcaagtgg | agcatcaggc | agaccoctcc | ttattgcttt | aattttgctc | atgtaattta | 780 |
| tgagtgtctt | ctgcttgatt | cctctgctgg | ccaggatttt | ttcgtagcga | tcaagccatg | 840 |
| aatgtaacgt | aacggaatta | tcactgttga | ttctcgctgt | cagaggcttg | tgtttgtgtc | 900 |
| ctgaaaataa | ctcaatgttg | gcctgtatag | cttcagtgat | tgcgattcgc | ctgtctctgc | 960 |
| ctaatccaaa | ctctttaccc | gtccttgggt | ccctgtagca | gtaatatcca | ttgtttctta | 1020 |
| tataaaggtt | aggggtaaa | tcccggcgct | catgacttcg | ccttcttccc | atttctgatc | 1080 |
| ctcttcaaaa | ggccacctgt | tactggtcga | tttaagtcaa | cctttaccgc | tgattcgtgg | 1140 |
| aacagatact | ctcttccatc | cttaaccgga | ggtgggaata | tcctgcattc | ccgaacccat | 1200 |
| cgacgaactg | tttcaaggct | tcttggacgt | cgctggcgtg | cgttccactc | ctgaagtgtc | 1260 |
| aagtacatcg | caaagtctcc | gcaattacac | | | | 1290 |

<210> SEQ ID NO 35
<211> LENGTH: 351
<212> TYPE: DNA
<213> ORGANISM: Artificial Sequence
<220> FEATURE:
<223> OTHER INFORMATION: Description of Artificial Sequence: Synthetic
      DNA fragment sequence

<400> SEQUENCE: 35

| | | | | | |
|---|---|---|---|---|---|
| caaaaagagt | ttgtagaaac | gcaaaaaggc | catccgtcag | gatggccttc | tgcttaattt | 60 |
| gatgcctggc | agtttatggc | gggcgtcctg | cccgccaccc | tccgggccgt | tgcttcgcaa | 120 |
| cgttcaaatc | cgctcccggc | ggatttgtcc | tactcaggag | agcgttcacc | gacaaacaac | 180 |
| agataaaacg | aaaggcccag | tctttcgact | gagccttttcg | ttttatttga | tgcctggcag | 240 |
| ttccctactc | tcgcatgggg | agaccccaca | ctaccatcgg | cgctacggcg | tttcacttct | 300 |
| gagttcggca | tggggtcagg | tgggaccacc | gcgctactgc | cgccaggcaa | a | 351 |

METHOD FOR DETERMINING METABOLIC FLUX AFFECTING SUBSTANCE PRODUCTION

TECHNICAL FIELD

The present invention relates to a method for determining a metabolic flux affecting substance production, a method for creating a bacterial strain using the determination method, a program for executing the determination method and a recording medium storing the program.

BACKGROUND ART

A metabolic flux analysis, which is also referred to as a flux balance analysis, is a technique for predicting intracellular metabolic flux distributions by construction of a stoichiometric model of intracellular biochemical reactions and linear optimization. This technique has been used in research into the abilities of biochemical reaction systems in microorganisms or for predictiing intracellular metabolic flux distributions under different external conditions (Non-patent documents 1, 2 and 3). It has also been reported that a stoichiometric model was constructed for *Escherichia coli* (Non-patent documents 4 and 5). Also known is an example of using such a stoichiometric model in metabolic engineering for lysine production for *Corynebacterium glutamicum*, which is used in amino acid production (Non-patent document 6). In addition, a large number of theoretical or experimental methods for metabolic flux analyses and their applications have been reported (Non-patent documents 7, 8, Patent documents 1, 2 and 3). Patent document 1 discloses a method for predicting a gene required for growth based on a stoichiometric model. Patent document 2 discloses a technique for genetically and evolutionarily changing cells to impart optimal functions to the cells. Further, Patent document 3 discloses a method for applying limitations of qualitative kinetic information, limitations of qualitative control information and limitations based on DNA microarray experimental data under different conditions to a stoichiometric model. Although all of these are methods for predicting more desirable intracellular metabolic flux distributions, no method has been disclosed for theoretically predicting a flux as a target for directly improving cellular substance production.

<Non-Patent Document 1>
Varma, A. and Palsson, B. O. Appl. Environ. Microbiol. 60:3724-3731, 1994

<Non-Patent Document 2>
Schilling, C. H. et al., Biotechnol. Prog., 15:288-295, 1999

<Non-Patent Document 3>
Schilling, C. H. et al., Biotechnol. Prog., 15:296-303, 1999

<Non-Patent Document 4>
Pramanik, J. and Keasling, J. D., Biotechnol. Bioeng., 56:398-421, 1997

<Non-Patent Document 5>
Ibarra, R. U. et al., Nature, 420:186-189, 2002

<Non-Patent Document 6>
Vallino, J. J. and Stephanopoulos, G., Biotechnol. Bioeng., 41:633-646, 1993

<Non-Patent Document 7>
Wiechert, W., Journal of Biotechnology, 94:37-63, 2002

<Non-Patent Document 8>
Wiechert, W., Metabolic Engineering, 3:195-205, 2001

<Patent Document 1>
International Publication No. WO00/46405

<Patent Document 2>
International Publication No. WO02/061115

<Patent Document 3>
International Publication No. WO02/055995

DISCLOSURE OF THE INVENTION

The present invention provides a method for predicting an effective way for modification of a cell by using an intracellular metabolic flux analysis to improve yield of a target product or biomass and productivity of a product in production of a substance, such as amino acids, organic acids and nucleic acids, using cells such as those of a microorganism. More specifically, the present invention provides a method for determining a metabolic flux affecting substance production, a method for producing a bacterial strain using the determination method, a program for executing the determination method and a recording medium storing the program.

In view of the aforementioned objects, the inventors of the present invention assiduously studied and as a result, they found that a metabolic flux affecting substance production could be determined by selecting the same number of free fluxes as the degree of freedom of a stoichiometric matrix calculated based on formulas of biochemical reactions from a substrate through a desired produced substance (substance to be produced), calculating metabolic flux distributions from each of random combinations of the free fluxes in a number sufficient for a statistical analysis based on the stoichiometric matrix, and obtaining a regression equation which includes a minimum number of free fluxes which correlate to the substance production from the calculated metabolic flux distributions based on a statistical analysis. The present invention was accomplished based on the aforementioned findings and includes at least the following:

(1) A method for determining at least one metabolic flux affecting substance production using cells, includes the steps of:

1) creating a stoichiometric matrix based on formulas of biochemical reactions of a substrate through a desired produced substance, 2) selecting the same number of independent metabolic fluxes from all metabolic fluxes as the degree of freedom of the stoichiometric matrix as free fluxes, 3) creating a sufficient number of random combinations of the free fluxes for a statistical analysis and calculating a metabolic flux distribution from each created combination based on the stoichiometric matrix, 4) obtaining a regression equation, including a minimum number of free fluxes that shows a correlation with substance production from the calculated metabolic flux distributions by a multivariate statistical analysis, and 5) determining at least one metabolic flux affecting substance production based on a coefficient in the obtained regression equation.

(2) The method according to (1), wherein the statistical analysis is a multivariate linear regression analysis.

(3) The method according to (1) or (2), wherein the cells are those of a microorganism having an ability to produce an amino acid, a nucleic acid or an organic acid.

(4) A method for creating a bacterial strain having a substance producing ability, which comprises modifying a bacterial strain so that, among the metabolic fluxes affecting substance production determined by the method as defined in any of (1) to (3) or any metabolic flux belonging to the same independent metabolic flux group including the metabolic fluxes, when the metabolic fluxes show a positive correlation with the substance production, an activity responsible therefor is increased, or when the metabolic fluxes show a negative correlation with the substance production, an activity responsible therefor is attenuated, or both.

(5) A method for producing a substance, which comprises cultivating the bacterial strain created by the method as defined in (4) in a culture medium, to produce and accumulate the substance in the culture medium or cells of the bacterium, and collecting the substance from the culture medium or the cells, wherein the substance is an amino acid, a nucleic acid, or an organic acid.

(6) A program for determining at least one metabolic flux affecting substance production using cells, which allows a computer to execute a metabolic flux determination method comprising the procedures of:
1) creating a stoichiometric matrix based on formulas of biochemical reactions from a substrate through a desired produced substance,
2) selecting the same number of independent metabolic fluxes from all metabolic fluxes as the degree of freedom of the stoichiometric matrix as free fluxes,
3) creating a sufficient number of random combinations of the free fluxes for a statistical analysis and calculating a metabolic flux distribution from each created combination based on the stoichiometric matrix,
4) obtaining a regression equation including a minimum number of free fluxes that shows a correlation with substance production from the calculated metabolic flux distributions by a multivariate statistical analysis, and
5) determining at least one metabolic flux affecting substance production based on a coefficient in the obtained regression equation.

(7) A computer-readable recording medium, which records the program as defined in (6).

BEST MODE FOR CARRYING OUT THE INVENTION

Figure 1:
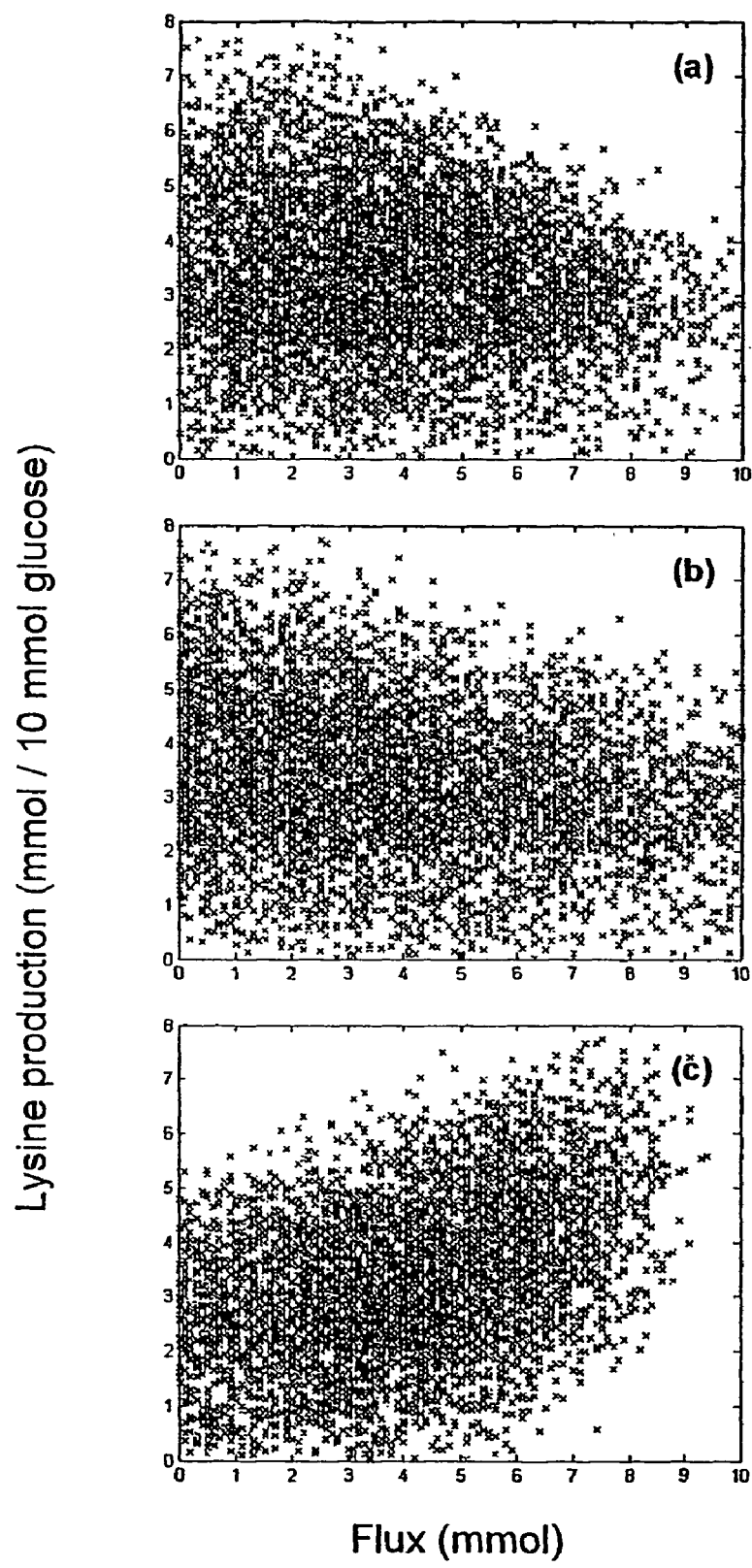
FIG. 1 is a plot showing lysine production as a function of different values of free fluxes by using a dataset of 5000 random flux distributions. The lysine yields are shown for (a) isocitrate lyase flux, (b) malic enzyme flux and (c) PEP carboxylase flux.

Hereinafter, the present invention will be explained in detail.

<1> Determination Method of the Present Invention

The determination method of the present invention is a method for determining a metabolic flux affecting substance production using a cell.

The metabolic flux used in the present invention is expressed as a metabolic reaction rate (flux) derived from a stoichiometric model of intracellular biochemical reactions and the law of mass action between metabolites; meanwhile, the metabolic flux distribution used herein consists of all the metabolic fluxes wherein each metabolic flux is assigned to each biochemical reactions.

The cell used in the present invention is not particularly limited so long as it is used in substance production. Examples thereof include various cultured cells, fungi, yeasts, various bacteria and so forth. It is preferably that of a microorganism having an ability to produce a useful compound, for example, an amino acid, a nucleic acid or an organic acid. As the microorganism having an ability to produce an amino acid, a nucleic acid or an organic acid, *Escherichia coli*, *Bacillus* bacteria, coryneform bacteria and so forth are preferably used. A microorganism having an amino acid-producing ability and/or an organic acid-producing ability is more preferred. Such microorganisms having an ability to produce an useful compound, for example, are shown in EP-A 1016710 for *Escherichia coli*, JP-A 2003-259861 for *Bacillus* bacteria, and WO 00/18935 for coryneform bacteria. The microorganism is modified based on the information about the metabolic flux affecting substance production that can be obtained by the present invention so that its substance-producing ability should be improved.

In the first step of the determination method of the present invention, a stoichiometric matrix is created based on the biochemical reaction formulas of a substrate through a desired substance product.

The biochemical reactions refer to a process in which intracellular metabolites are converted by enzymatic reactions in the cell, and which have been compiled in various databases according to organism type. For example, the website of Kyoto Encyclopedia of Genes and Genomes (KEGG) can be accessed for reference.

The substrate is a substance usually used by the cell as a carbon source, and examples thereof include glucose, sucrose, fructose and so forth.

The substance product includes not only a single kind of metabolite, but also an aggregate of metabolites, such as a biomass (cell body). Substance production is usually evaluated as a production rate of a substance. In particular, when the desired substance is a biomass, it is evaluated as a biomass yield. The biomass yield represents efficiency of conversion from substrates such as glucose into cell components such as protein, carbohydrate, nucleic acid or lipid.

The stoichiometric matrix is a matrix usually used in a metabolic flux analysis, and can be created by listing formulas of biochemical reactions of a substrate through a desired product substance by typical methods used in a metabolic flux analysis. Such methods, assuming a quasi-steady state of an intracellular metabolic intermediate, are generally known (Savinell, J. M. and Palsson, B. O. J., Theor. Biol., 154:421-454, 1992; Vallino, J. J. and Stephanopoulos, G., Biotechnol. Bioeng., 41:633-646, 1993). When reaction formulas are listed, reaction pathways may be simplified by assuming a series of reactions without branching as one reaction, or assuming metabolites converted by a reaction at a high metabolic rate before and after the reaction as one metabolite and so forth. When the substance product is a biomass, a stoichiometric matrix can be described by listing biochemical reactions which lead to cell components.

In the second step of the determination method of the present invention, the same number of independent metabolic fluxes as the degree of freedom of the aforementioned stoichiometric matrix are selected as free fluxes from all metabolic fluxes.

Independent fluxes are a set of fluxes that should be specified to uniquely define fluxes in the metabolism network system as defined by a stoichiometric equation.

The method for setting free fluxes is not particularly limited so long as the same number of independent metabolic fluxes as the degree of freedom of the system to be analyzed can be selected. Although the independence of arbitrarily selected fluxes may be confirmed, the SIMS matrix (steady-state internal metabolic stoichiometric matrix) proposed by Reder can also be used (Reder, C. J., Theor. Biol., 135:175-201, 1988). In this method, specific groups of metabolic fluxes in the same number as the degree of freedom of the aforementioned stoichiometric matrix are determined among metabolic flux groups determined based on the aforementioned biochemical reaction formulas, and a metabolic flux is determined as a free flux from each selected metabolic flux group. Determining specific groups among the flux groups ensures that any flux in a group can be changed without affecting the fluxes in other groups. Therefore, it becomes possible to select one flux from each group as an independent free flux. When a free flux is selected from a flux group, a flux close to a branch point is preferably selected.

In the third step of the determination method of the present invention, random combinations of free fluxes in a number sufficient for a statistical analysis are created, and a metabolic flux distribution is calculated from each created combination based on the aforementioned stoichiometric matrix.

Random combinations of free fluxes can be created by giving random values to the free fluxes selected in the previous step to create a dataset of combinations of different flux distributions. The method for giving random values to the free fluxes is not particularly limited so long as a method which generates combinations of free fluxes within a specific border is chosen. Said specific border is set to give biologically feasible values in later calculations. If the number of free fluxes is the same as the degree of freedom of the specified stoichiometric matrix, a unique metabolic flux distribution can be solved. For the solution, a matrix operation using an inverse matrix is commonly performed, and all fluxes are preferably normalized into, for example, certain amounts of substrate. When the substrate is glucose, all flux values can be represented, for example, with values per 10 mmol of glucose uptake. The solutions of metabolic flux distributions obtained from random free flux values as described above must be biologically significant. That is, all fluxes of non-reversible reactions must be 0 or more, and biomass forming fluxes must be 0 or more. To obtain combinations of more desirable free fluxes, conditions based on theoretical and/or empirical knowledge in substance production using cells can also be added. The number of combinations to be created, that is, the number of biologically significant flux distributions to be calculated, is not particularly limited so long as it is sufficient for a statistical analysis. Three or five values are usually used for one free flux. Therefore, when there are n free fluxes, there are about to the n-th power of the number of the values for one free flux of combinations. For example, when three values are used for one free flux, there are 3 to the n-th power ($3^n$) of combinations. That is, about 2,200 combinations can be used for seven free fluxes (n=7). Alternatively, since the number of values for each free flux in the dataset of biologically significant flux distributions can change depending on selected free fluxes or additional conditions, the number of combinations that may be used is about 3 to the n-th power ($3^n$) to about 5 to the n-th power ($5^n$) in total for n of free fluxes. To obtain solutions of biologically significant flux distributions in such a number, it is typical to start from combinations of random free fluxes using 6 to 10 values for one free flux, that is, combinations of free fluxes of 6 to the n-th power ($6^n$) to 10 to the n-th power ($10^n$).

In the fourth step of the determination method of the present invention, a regression equation including a minimum number of free fluxes that show a correlation with substance production is obtained from the metablic flux distributions (dataset of metabolic flux distributions) by a multivariate statistical analysis.

By performing a multivariate statistical analysis for the dataset of flux distributions calculated from random combinations of the free fluxes obtained in the previous step, a regression equation including a minimum number of free fluxes that shows a correlation with substance production can be obtained. The multivariate statistical analysis (including multivariate non-linear regression analysis and multivariate linear regression analysis) can be performed by using any technique so long as a technique is chosen which can examine correlations of free flux combinations with substance production. However, a multivariate linear regression analysis is useful. This method is described in, for example, Kachigan, S. K., Chapter 4, Regression Analysis in Multivariate Statistical Analysis 2nd Ed., Radius Press, New York, pp. 160-193.

The expression "shows a correlation with substance production" means that the coefficient of determination is significantly large, and "being significantly large" usually means that the coefficient of determination $R^2$ is 0.8 or higher, preferably 0.9 or higher.

A regression equation, including a minimum number of free fluxes (terms) that shows a correlation with substance production, may be obtained by successively changing the number of terms to obtain a regression equation. Such an equation that shows the largest coefficient of determination, including each number of terms, and enables selecting a regression equation including a minimum number of terms that shows a significantly large coefficient of determination. Alternatively, a regression equation may be obtained with the total terms except for one term to examine the degree of decrease in the coefficient of determination due to the exclusion of the term; the same procedure may be repeated with terms except for the term showing decrease in a small degree of the coefficient of determination, as the total terms; and when a regression equation that shows a correlation with substance production can no longer be obtained, the regression equation obtained immediately therebefore may be selected.

Although these mathematical procedures can be individually programmed, they can be readily performed by using commercially available mathematical computation programs such as MatLab® (trade name, MathWorks) and Mathematica® (trade name, Wolfram Research).

In the fifth step of the determination method of the present invention, a metabolic flux affecting substance production is determined based on coefficients in the obtained regression equation.

Contributions of free fluxes to substance production using cells such as microorganisms, in particular, biomass yield or product substance yield, which are important in substance production, can be determined by utilizing the regression equation obtained in the previous step. That is, free fluxes that appear in the regression equation can be determined as those affecting substance production. Furthermore, since coefficients in the regression equation represent the magnitude of contribution, free fluxes having a substantially large coefficient (when fluxes are normalized, free fluxes having a large absolute value of relative coefficient) can be determined as metabolic fluxes that greatly affect substance production.

The determination method of the present invention can provide information which is important for improving bacterial strains, i.e., which free flux greatly influences the production of a target substance, and whether a free flux has a positive or negative effect on the production of a target substance. A flux that needs to be changed to favorably affect the yield and productivity of target product can also be predicted.

<2> Creation Method of the Present Invention

The creation method of the present invention is a method for creating a bacterial strain having a substance producing ability. The method comprises modifying a bacterial strain so that, among the metabolic fluxes affecting substance production determined by the determination method of the present invention or any metabolic flux belonging to the same independent metabolic flux group including the metabolic fluxes, when the metabolic fluxes show a positive correlation with the substance production, an activity responsible therefore is increased, and/or when the metabolic fluxes show a negative correlation with the substance production, an activity responsible therefore is attenuated.

In addition to the metabolic fluxes determined by the determination method of the present invention, activity responsible for any metabolic flux belonging to the same independent metabolic flux group including the metabolic flux may be modified, because it is considered that metabolic fluxes included in the same metabolic flux group also have the same effect. However, it is expected that ease of actual metabolic engineering techniques and the magnitude of effect of changes in enzymatic activity vary depending on the enzymes responsible for fluxes. If the labor and effect upon improvement of the production bacteria are considered, it can be expected that a flux close to a branch point would be effective. For example, in the pentose phosphate pathway, it is expected that selection of glucose-6-phosphate dehydrogenase would be as effective as selection of transketolase.

Various methods are known for changing activity responsible for a specific flux. As methods for enhancing an enzymatic activity, increase in copy number of a gene coding for an enzyme by using extrachromosomal DNA such as plasmid or increase in copy number on a chromosome, introduction of a mutation into a promoter of the gene coding for the enzyme to enhance activity, and replacement of a promoter with a stronger one are known. As methods for attenuating an enzymatic activity, disruption of a gene coding for an enzyme or introduction of a mutation into the gene to attenuate activity, introduction of a mutation into a promoter of the gene coding for the enzyme to attenuate activity, and replacement of a promoter with a weaker one are known. By these methods, an activity responsible for a specific flux can be changed to improve yield or productivity of a target product. For example, as shown in the examples described later, it can be expected that bacterial strains with an improved lysine-producing ability can be created by enhancing activity of phosphoenolpyruvate carboxylase in lysine production using *Escherichia coli*, and International Publication No. WO01/53459 discloses an example of improvement of lysine production by enhancing phosphoenolpyruvate carboxylase activity. Therefore, it has been verified that the creation method of the present invention based on the determination method of the present invention is extremely useful.

<3> Production Method of the Present Invention

The method of the present invention is a method for producing an amino acid, a nucleic acid or an organic acid, which method comprises the steps of cultivating the bacterium having an ability to produce amino acid, nucleic acid or organic acid, in a medium, to cause accumulation of amino acid, nucleic acid or organic acid in the medium or cells of the bacterium, and to collect the amino acid, the nucleic acid or the organic acid from the medium or the cells. The term "nucleic acid" used herein means a nucleoside or a nucleotide.

The culture medium used in the present invention may be a medium typically used for fermentation production of an amino acid, a nucleic acid or an organic acid using a microorganism. An ordinary medium including a carbon source, a nitrogen source, inorganic ions and the other organic components, if necessary, may be used. As the carbon source, various saccharides such as glucose, sucrose, lactose, galactose, fructose, and starch hydrolysate, various alcohols such as glycerol and sorbitol, and various organic acids such as fumaric acid, citric acid and succinic acid may be used. As the nitrogen source, various inorganic ammonium salts such as ammonium sulfate, ammonium chloride and ammonium phosphate, organic nitrogen such as soybean hydrolysate, ammonia gas and aqueous ammonia and the like may be used. As a trace organic nutrient, it is desirable to add required substances such as vitamin $B_1$, homoserine, or yeast extract and the like. In addition, a trace amount of potassium phosphate, magnesium sulfate, iron ion, manganese ion may be added. The medium used for culture may be either a synthetic medium or a natural medium, so long as the medium includes a carbon source and a nitrogen source and inorganic ions and, if necessary, trace organic nutrients.

The cultivation is preferably performed under aerobic conditions for one to seven days at a temperature of 24 to 37° C., and a pH of 5 to 9. The pH of the culture can be adjusted with an inorganic or organic acid or alkaline substance, for example, ammonia gas and the like. The collection an amino acid, a nucleic acid or an organic acid from the culture medium may be performed by usual methods, such as an ion-exchange resin method, precipitation and the other known methods, and combinations thereof. When the amino acid, the nucleic acid or the organic acid accumulates in cells, the amino acid, the nucleic acid or the organic acid may be collected by an ion-exchange resin method or the like from a supernatant obtained by disrupting the cells by ultrasonic or the like, and removing cell debris by centrifugation.

<4> Program of the Present Invention

The present invention also provides a program for executing the determination method of the present invention. The program of the present invention is a program for determining at least one metabolic flux affecting substance production using cells, which allows a computer to execute a metabolic flux determination method comprising the procedures of:

1) creating a stoichiometric matrix based on formulas of biochemical reactions from a substrate through a desired produced substance, 2) selecting the same number of independent metabolic fluxes from all metabolic fluxes as the degree of freedom of the stoichiometric matrix as free fluxes, 3) creating sufficient number of random combinations of the free fluxes for a statistical analysis and calculating a metabolic flux distribution from each created combination based on the stoichiometric matrix, 4) obtaining a regression equation including a minimum number of free fluxes that shows a correlation with substance production from the calculated metabolic flux distributions by a multivariate statistical analysis, and 5) determining at least one metabolic flux affecting substance production based on a coefficient in the obtained regression equation.

Further, another aspect of the present invention relates to a computer-readable recording medium, characterized in that it records the aforementioned program.

Figure 3:
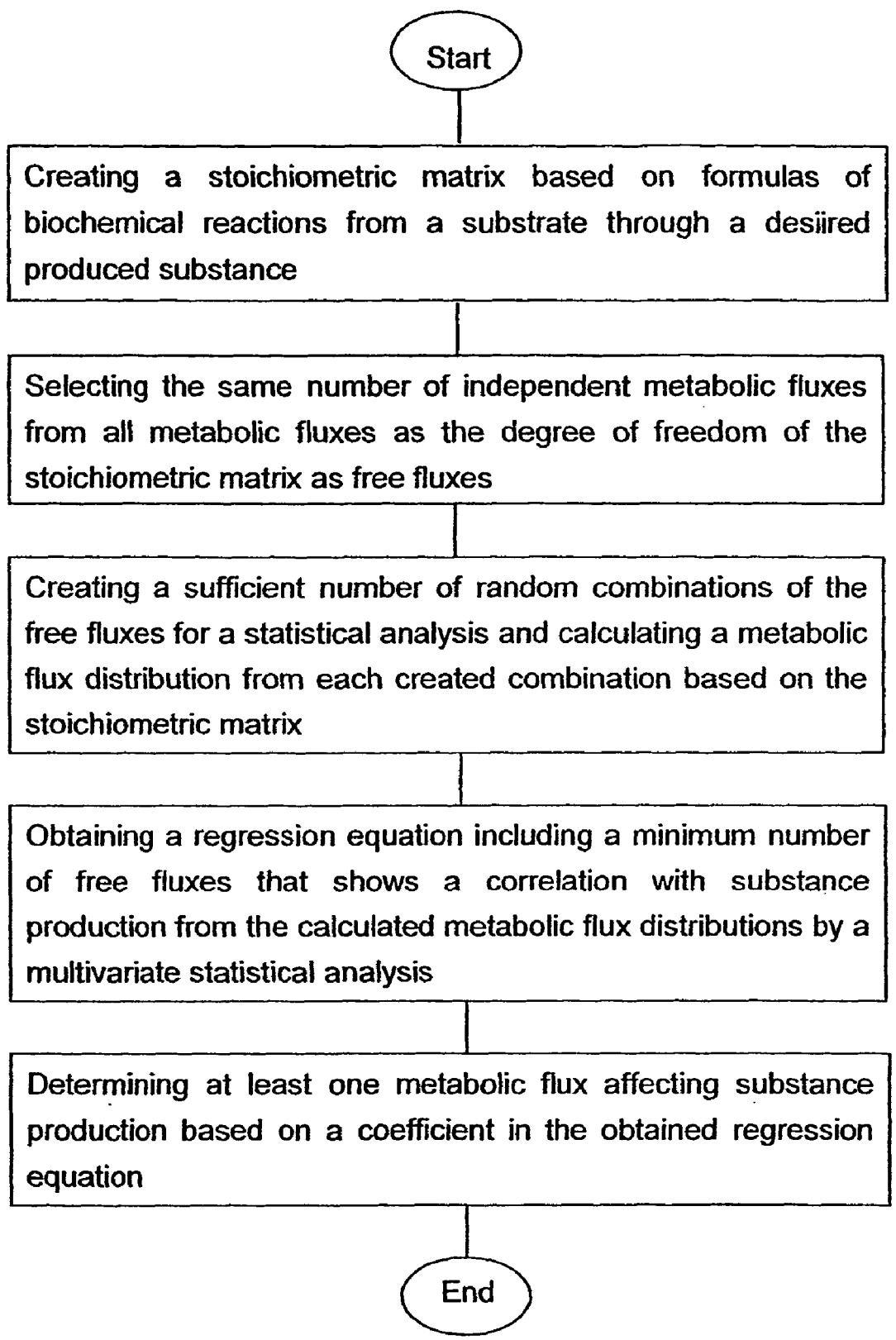
FIG. 3 shows a flowchart of a metabolic flux determination program.
Figure 4:
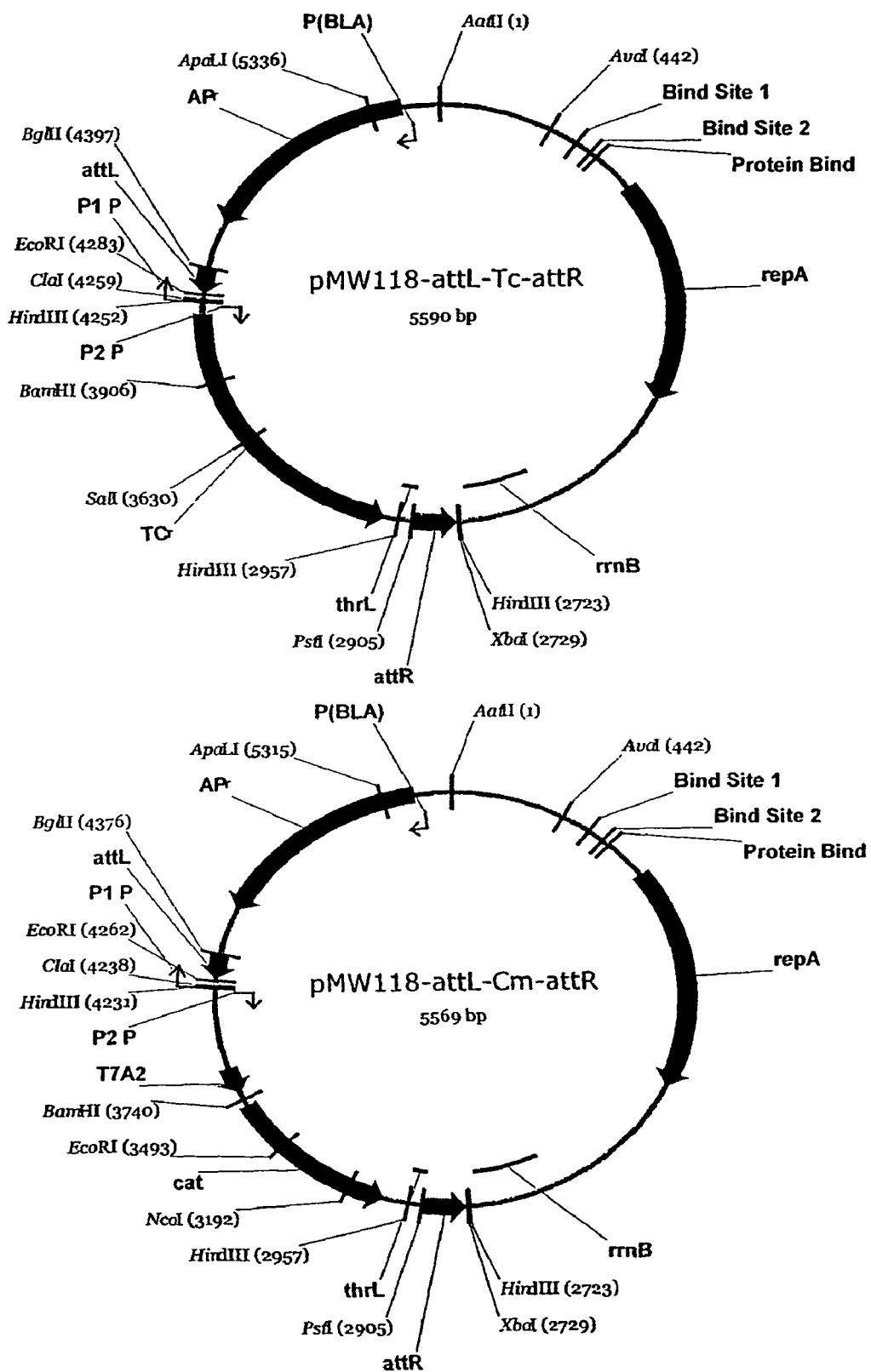
FIG. 4 shows the structures of pMW118-attL-Tc-attR and pMW118-attL-Cm-attR.
Figure 5:
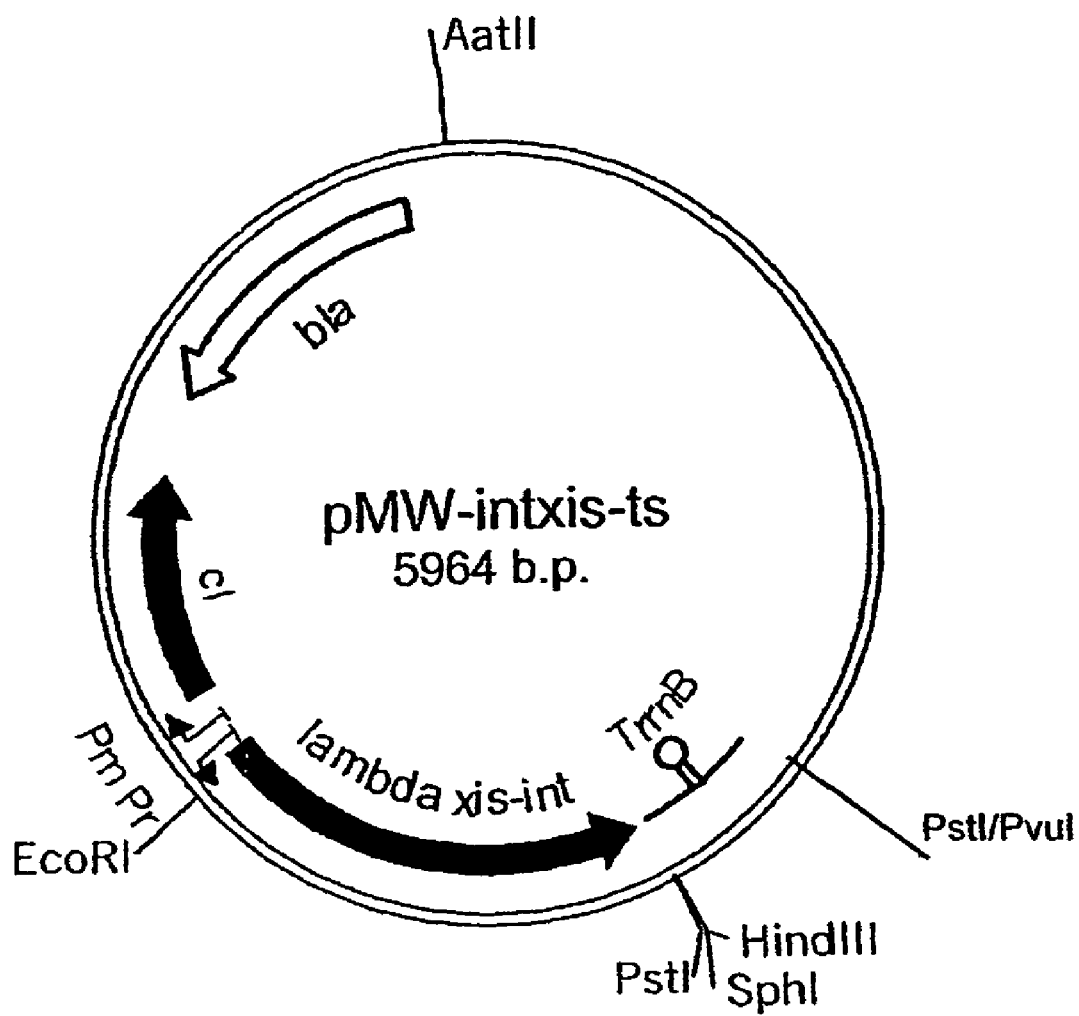
FIG. 5 shows the structure of pMW-intxis-ts.

A flowchart of the program of the present invention is shown in FIG. 3. Each procedure is a procedure for executing each of the steps 1) to 5) in the determination method of the present invention. The programs for allowing the computer to execute these procedures can be created according to a usual programming method.

Further, the program according to the present invention can also be stored in a computer-readable recording medium. The term "recording medium" used herein includes arbitrary "removable physical media" such as Floppy (registered trade name) disc, magneto-optical disc, ROM, EPROM, EEPROM, CD-ROM, MO and DVD, arbitrary "fixed physical media" such as ROM, RAM and HD built in various computer systems and "communication media" for temporarily storing a program such as communication circuits and carrier waves for transmitting a program via a network represented by LAN, WAN and the Internet.

Further, the "program" is one for processing data written in an arbitrary language or operation notation, and its format such as source code or binary code is not limited. The "program" is not necessarily limited to a single program, and includes a program described in a distributed architecture comprising two or more modules or libraries or achieves its function by cooperating with a separate program represented by Operating System (OS). Well-known configurations and procedures can be used as specific configurations for reading the program stored in a recording medium, reading procedures, installation procedures after reading and so forth in each device shown in the embodiments.

EXAMPLES

The present invention is further described in detail by referent to examples.

Example 1

Determination of Metabolic Flux with Respect to L-Lysine (1) Creation of Stoichiometric Matrix A stoichiometric equation for calculating a metabolic flux was constructed by assuming a quasi-steady state of intracellular metabolic intermediates (Savinell, J. M. and Palsson, B. O. J., Theor. Biol., 154:421-454, 1992; Vallino, J. J. and Stephanopoulos, G., Biotechnol. Bioeng., 41:633-646, 1993). The reaction formulas included in this model are as shown in Table 2. Descriptions of the abbreviations used in the present invention are listed in Table 1. Some reactions without branching were consolidated to simplify the formulas. Since the pentose phosphate pathway is complicated, it was represented by two formulas. Reported data was used for the component ratio of biomass (Neidhardt, F. C. et al., Physiology of the Bacterial Cell., Sinauer Associates, Massachusetts, 1990) and the biomass was represented by using the reaction formula [68]. The degree of freedom of the stoichiometric matrix in this model was 7.

TABLE 1

| 3PG | 3-Phospho-D-glyceric acid |
|---|---|
| AcCoA | Acetyl coenzyme A |
| AcOH | Acetic acid |
| aIVA | A-Keto-isovaleric acid |
| aKG | 2-Oxoglutaric acid |
| Ala | Alanine |
| ALC | Acetohydroxy acid |
| Arg | Arginine |
| ASA | Aspartic acid semialdehyde |
| Asn | Asparagine |
| Asp | Aspartic acid |
| CHR | Chorismic acid |
| Cit | Citric acid |
| CO2 | Carbon dioxide |
| CoA | Coenzyme A |
| Cys | Cysteine |
| DDP | Dihydrodipicolinic acid |
| E4P | Erythrose-4-phosphate |
| F6P | Fructose-6-phosphate |
| FBP | Fructose bisphosphate |
| Form | Formic acid |
| Fum | Fumaric acid |
| G6P | Glucose-6-phosphate |
| GAP | Glyceraldehyde phosphate |
| Glc | Glucose |
| Gln | Glutamine |
| Glu | Glutamic acid |
| Gly | Glycine |
| Glyox | Glyoxylic acid |
| His | Histidine |
| Hse | Homoserine |
| Ile | Isoleucine |
| Ind | Indole glycerol phosphate |
| Isocit | Isocitric acid |
| Leu | Leucine |
| Lys | Lysine |
| Lysext | Lysine product (extracellular) |
| Mal | Malic acid |
| Met | Methionine |
| mDAP | meso-Diaminopimelic acid |
| mTHF | Methyl tetrahydrofolate |
| NH3 | Ammonia |
| OAA | Oxaloacetatic acid |
| PEP | Phosphoenolpyruvic acid |
| Phe | Phenylalanine |
| PPA | Prephenic acid |
| Pro | Proline |
| PRPP | Phophoribosyl pyrophosphate |
| Pyr | Pyruvic acid |
| R5P | Ribose-5-phosphate |
| Ribu5P | Ribulose-5-phosphate |
| SDAP | N-Succinyl-L-2,6-diaminoheptanedioate |
| SKA | Shikimic acid |
| Sed7P | D-Sedoheptulose-7-phosphate |
| Ser | Serine |
| Suc | Succinic acid |
| SucCoA | Succinyl coenzyme A |
| THDP | Tetrahydrodipicolinic acid |
| THF | Tetrahydrofolic acid |
| Thr | Threonine |
| Trp | Tryptophan |
| Tyr | Tyrosine |
| Val | Valine |
| X5P | Xylulose-5-phosphate |

TABLE 2

List of used reaction formulas. Reversible reactions are marked with r.

[1]   Glc + PEP --> G6P + Pyr
[2]   G6P + 2NADP --> Ribu5P + 2NADPH + CO2
[3] r Ribu5P --> R5P
[4] r Ribu5P -->X5P
[5] r X5P + R5P --> Sed7P + GAP
[6] r Sed7P + GAP --> E4P + F6P
[7] r X5P + E4P --> F6P + GAP TABLE 2-continued List of used reaction formulas. Reversible reactions are marked with r.

[8] r    G6P --> F6P
[9] r    F6P + ATP --> FBP + ADP
[10] r   FBP --> 2GAP
[11] r   GAP + NAD + ADP --> 3PG + NADH + ATP
[12] r   3PG -->PEP
[13]     PEP + ADP --> Pyr + ATP
[14]     Pyr + NAD + CoA --> AcCoA + NADH + CO2
[15]     PEP + CO2 --> OAA
[16]     AcCoA + ADP --> AcOH + ATP + CoA
[17]     AcCoA + OAA --> Cit + CoA
[18] r   Cit --> Isocit
[19] r   Isocit + NADP --> aKG + NADPH + CO2
[20]     aKG + NADPH + NH3 --> Glu + NADP
[21]     aKG + NAD + CoA --> SucCoA + NADH + CO2
[22] r   SucCoA + ADP --> Suc + ATP + CoA
[23] r   Suc + FAD --> Fum + FADH
[24] r   Fum --> Mal
[25] r   Mal + NAD --> OAA + NADH
[26]     OAA + Glu --> Asp + aKG
[27]     Asp + ATP + NADPH --> ASA + ADP + NADP
[28]     ASA + Pyr --> DDP
[29]     DDP + NADPH --> THDP + NADP
[30]     THDP + SucCoA + Glu --> SDAP + aKG + CoA
[31]     SDAP --> mDAP + Suc
[32]     mDAP --> Lys + CO2
[33] r   Glu + ATP + NH3 --> Gln + ADP
[34]     Glu + 2NADPH + ATP --> Pro + 2NADP + ADP
[35]     Glu + 5ATP + NADPH + Gln + Asp + AcCoA + CO2 --> Arg + 5ADP + NADP + aKG + Fum
[36]     ASA + NADPH --> Hse + NADP
[37]     Hse + SucCoA + Cys + mTHF --> Met + Suc + CoA + THF + Pyr + NH3
[38]     Hse + ATP --> Thr + ADP
[39]     Thr + Glu + NADPH + Pyr --> Ile + aKG + NADP + NH3 + CO2
[40] r   3PG --> Ser
[41] r   Ser + THF --> Gly + mTHF
[42] r   PEP + E4P + NADPH --> SKA + NADP
[43]     CHR --> PPA
[44]     PPA + NAD + Glu --> Tyr + NADH + CO2 + Akg
[45]     PPA + Glu --> Phe + CO2 + aKG
[46]     CHR + R5P + 2ATP + Gln --> Ind + Glu + Pyr + CO2 + GAP + 2ADP
[47]     2Pyr --> ALC
[48]     aIVA + Glu --> Val + aKG
[49]     Val + Pyr --> ALA + aIVA
[50]     aIVA + AcCoA + NAD + Glu --> Leu + NADH + CO2 + aKG + CoA
[51]     PRPP + ATP + Gln + Glu + 2NAD --> His + ADP + Glu + aKG + 2NADH
[52]     Ser + AcCoA + H2S --> Cys + AcOH
[53]     SKA + PEP + ATP --> CHR + ADP
[54]     Ind + Ser --> Trp
[55]     ALC + NADPH --> aIVA + NADP + CO2
[56] r   NADH --> NADPH
[57]     2NADH + O2 + 2ADP --> 2ATP + 2NAD
[58]     2FADH + O2 + ADP --> ATP + 2FAD
[59] r   Asp + 2 ATP + NH3 --> Asn + 2 ADP
[60]     Isocit --> Glyox + Succ
[61]     AcCoA + Glyox --> Mal + CoA
[62]     Mal + NAD --> Pyr + CO2 + NADH
[63] r   R5P + 2 ATP --> PRPP + 2 ADP
[64]     mTHF + NADP --> NADPH + THF + Form
[65]     NAD + Gly + THF --> mTHF + NADH + CO2 + NH3
[66]     ATP --> ADP
[67]     Lys --> Lysext
[68]     Biomass synthesis (described below)
         RNA (21.33%)
         3.47 PRPP + 5.02 Gln + −5.02 Glu + 3.08 Gly + 6.17 Asp + 32.41 ATP + −32.41 ADP + 6.17 mTHF + −6.17 THF + 3.09 NAD + −3.09 NADH + 6.17 NADP + −6.17 NADPH + 1.16 CO2 + −3.47 Fum + −3.86 NH3
         DNA (3.23%)
         3.37 PRPP + 4.88 Gln + −4.88 Glu + 3 Gly + 6 Asp + 31.5 ATP + −31.5 ADP + 7.12 mTHF + −7.12 THF + 3 NAD + −3 NADH + 3.75 NADP + −3.75 NADPH + 1.12 CO2 + −3.37 Fum + −3.75 NH3
         Phospholipid (9.47%)

TABLE 2-continued

List of used reaction formulas. Reversible reactions are marked with r.

20.8 AcCoA + −20.8 CoA + 1.95 GAP + 0.65 Ser + 44.2 ATP + −44.2 ADP + 38.35 NADH + −38.35 NAD + −0.65 CO2
Peptidoglycan (2.60%)
1.94 F6P + 1.94 AcCoA + −1.94 CoA + 1.94 Gln + −1.94 Glu + 2.91 Ala + 0.97 PEP + 0.97 Lys + 6.97 ATP + −6.97 ADP + 0.97 NADPH + −0.97 NADP + −0.97 CO2
Lipopolysaccharide (3.54%)
0.91 R5P + 0.91 P6P + 0.91 PEP + 15.47 AcCoA + −0.91 AcOH + −0.91 Glu + 0.91 Gln + 32.76 ATP + 12.74 NADH
Protein (57.23%)
0.77 Gly + 0.96 Ala + 0.67 Val + 0.85 Leu + 0.44 Ile + 0.44 Ser + 0.48 Thr + 0.30 Phe + 0.26 Tyr + 0.01 Trp + 0.15 Cys + 0.22 Met + 0.54 Lys + 0.46 Arg + 0.16 His + 0.46 Asp + 0.52 Glu + 0.46 Asn + 0.52 Gln + 0.34 Pro
Glycogen (2.60%)
F6P + ATP (2) Selection of Free Fluxes and Creation of Random Combinations of Them Specific flux groups were determined according to the method of Reder (Reder, C. J., Theor. Biol., 135:175-201, 1988). A flux close to a branch point was selected from each group. Seven selected free fluxes are shown in Table 3. A unique solution for a flux balance can be obtained by specifying these 7 fluxes.

TABLE 3

List of free fluxes for obtaining random flux distribution

| Reaction number | Enzyme name or reaction pathway name |
|---|---|
| 2 | Glucose-6-phosphate dehydrogenase |
| 15 | PEP carboxylase |
| 16 | Acetic acid secretion |
| 60 | Isocitrate lyase (glyoxylate cycle) |
| 62 | Malic enzyme |
| 64 | Formic acid secretion |
| 66 | ATPase |

From the about 300,000 combinations of values for 7 random free fluxes, those infringing any limitation concerning reverse reactivity and those showing values for both of lysine and biomass not exceeding the threshold levels set at 20% of each maximum value were excluded. As a result, a dataset was created of 5000 metabolic flux distributions in a biologically significant specific region. The results were represented by values based on 10 mmol glucose uptake, and a matrix was created with 5000 rows corresponding to the random flux distributions and 68 columns each of which corresponded to a reaction flux.

(3) Correlation Analysis by Multivariate Analysis and Determination of Metabolic Fluxes Affecting Substance Production Multivariate linear regression of a condensed matrix including Z-scores of only columns corresponding to the 7 free fluxes was performed. The stepwise regression function of the MatLab statistical toolbox was used for multivariate linear regression. With this technique, biomass or lysine production can be derived with a linear function of 7 free fluxes. Identification of these 7 fluxes results in unique definition of the state of the system. Therefore, if all the 7 terms are used as parameters, the correlation coefficient becomes 1, indicating a complete fit. However, it is usually possible to obtain a relatively favorable fit with a fewer number of terms than in the equation. To try various combinations of terms, an equation showing the best fit for each number of contained terms was selected by using the stepwise function of the MatLab program. As for the biomass yield, a fit of $R^2=0.980$ was obtained with only 4 terms, isocitrate lyase (ICL), malic enzyme (MEZ), PEP carboxylase (PEPC) and ATPase. When the number of terms is further decreased, the $R^2$ value is markedly decreased, and any reasonable fit could not be obtained. When reaction fluxes are normalized to a value per 10 mmol glucose and used as the input, an accurate equation was represented as follows:

Biomass yield=1.552−0.194 (ICL)+0.184 (MEZ)−
0.194 (PEPC)−0.011 (ATPase)   Equation 1)

The lysine yield could be fit with a model including the same 4 parameters, and the result of $R^2=0.997$ was obtained. Further, even when the term for ATPase was excluded, $R^2$ decreased only to 0.856, and the fit was still favorable. Therefore, the following 3 parameters were used for the model of lysine.

Lysine yield=−1.694+1.176 (ICL)−1.095 (MEZ)+
1.162 (PEPC)   Equation 2)

Finally, the total carbon yield (C atoms) defined with the total number of carbon atoms directing to biomass and lysine could be fitted with $R^2=0.956$ by using only the term for ATPase with the following equation.

C atoms=34.3−0.314 (ATPase)   Equation 3)

Figure 2:
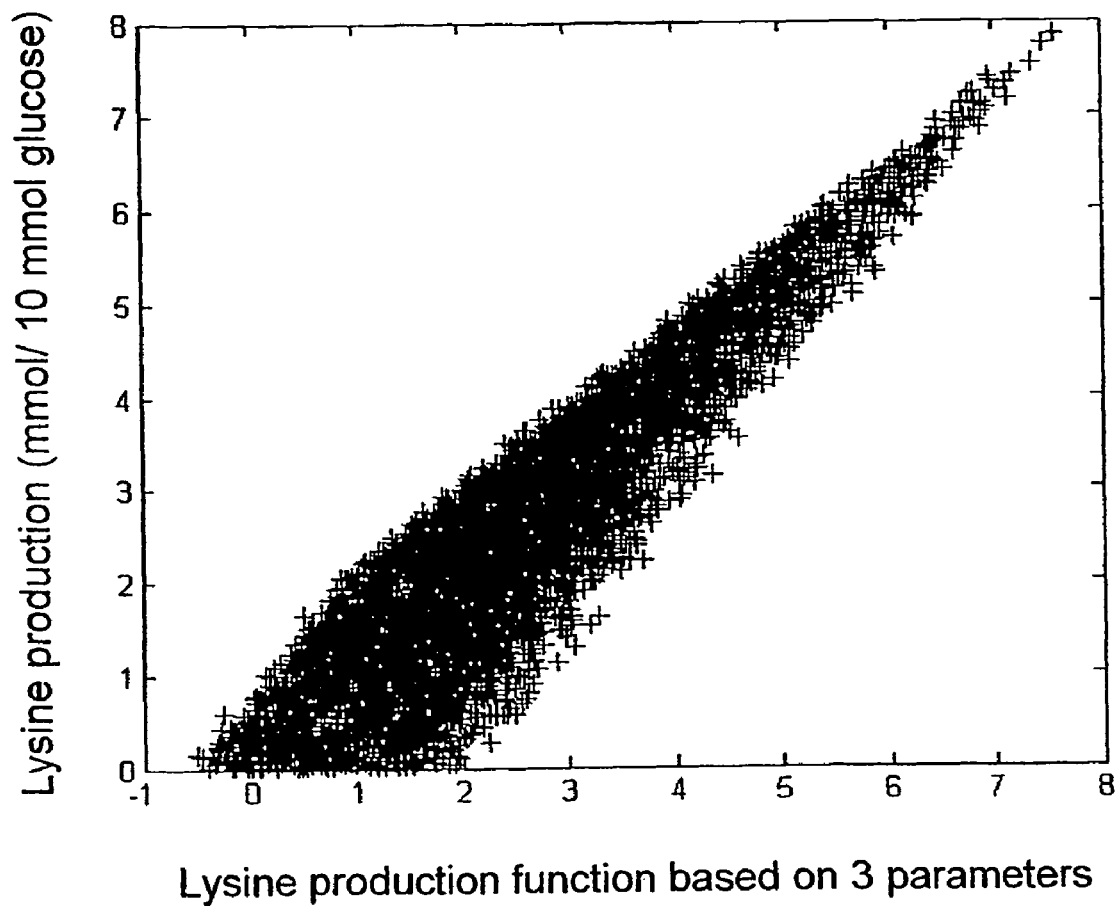
FIG. 2 is a plot showing lysine production as a function of values in equation 2 for a dataset of 5000 random flux distributions. The input value is a flux in mmol/hr based on 10 mmol/hr glucose flux.

These results revealed that the biomass yield positively correlated with the flux of malic enzyme, and that lysine production positively correlated with the fluxes of PEP carboxylase and isocitrate lyase (glyoxylate cycle). Usefulness of this regression analysis can be shown in FIGS. 1 and 2. When the fluxes of isocitrate lyase and malic enzyme are separately considered, no correlation with lysine production is observed as shown in FIG. 1, (a) and (b). However, when these fluxes are considered as a part of the regression equation 2), a correlation as shown in FIG. 2 can be observed, and the effect becomes clear. Thus, an invisible relationship between metabolic fluxes can be revealed with this technique. Yield of a target product can be improved by enhancing an activity responsible for a flux showing a positive correlation, and attenuating an activity responsible for a flux showing a negative correlation. That is, from this result, a guideline for improving bacterial strains could be obtained, and enhancement of the PEP carboxylase or isocitrate lyase activity or attenuation of the activity of malic enzyme showing a negative correlation is effective for lysine production. In fact, an example of creation of a bacterial strain showing an improved lysine producing ability by enhancing activity of PEP carboxylase in lysine production using *Escherichia coli* was disclosed in International Publication No. WO01/53459, and thus usefulness of the present invention has been supported.

Example 2

Determination of Metabolic Flux with Respect to L-Threonine

By the same method as in Example 1, an equation showing the best fit for each number of contained terms was selected with respect to L-threonine. As for the biomass yield, a fit of R=0.986 was obtained with only 4 terms, isocitrate lyase (ICL), malic enzyme (MEZ), PEP carboxylase (PEPC) and ATPase.

Biomass yield=1.260−0.101 (ICL)+0.093 (MEZ)−
0.101 (PEPC)−0.009 (ATPase)   Equation 4)

The threonine yield could be fit with a model including the same 3 parameters, and the result of $R^2=0.937$ was obtained.

Threonine yield=−1.432+1.090 (ICL)−1.080 (MEZ)+
1.087 (PEPC)   Equation 5)

These results revealed that the biomass yield positively correlated with the flux of malic enzyme, and that threonine production positively correlated with the fluxes of PEP carboxylase and isocitrate lyase (glyoxylate cycle). Therefore, with respect to threonine production, a guideline for improving bacterial strains could be also obtained, and enhancement of the PEP carboxylase or isocitrate lyase activity or attenuation of the activity of malic enzyme showing a negative correlation is effective for lysine production.

Example 3

Construction of Malic Enzyme-Deficient L-Lysine-Producing Bacterium

Strain WC196 was used as the L-lysine-producing strain of *Escherichia coli* which is resistant to AEC (S-(2-aminoethyl) cysteine) (International Publication No. WO 96/17930).

The malic enzyme from *Escherichia coli* includes one using NAD as coenzyme (EC 1.1.1.38) and one using NADP as coenzyme (EC 1.1.1.40). These enzymes are encoded by the sfcA and b2463 genes, respectively.

The sfcA and b2463 genes are deleted by a combination of the "red-driven integration" method, which was originally developed by Datsenko and Wanner (Proc. Natl. Acad. Sci. USA, 2000, 97, 6640-6645), and the excision system method, derived from lambda phage (J. Bacteriol. September 2002; 184(18): 5200-3. Interactions between integrase and excisionase in the phage lambda excisive nucleoprotein complex. Cho E H, Gumport R I, Gardner J F.). According to the red-driven integration method, a gene-disrupted strain can be constructed in one step by using PCR product obtained by using synthetic oligonucleotide primers designed to comprise a part of a targeted gene at its 5' terminal and a part of an antibiotic resistance gene at its 3' terminal. Furthermore, the integrated antibiotic resistance gene can be removed by further combining the excision system derived from lambda phage with the red-driven integration method.

(1) Disruption of sfcA Gene

As a PCR template, plasmid pMW118-attL-Cm-attR (its preparation is described below) was used. pMW118-attL-Cm-attR is a plasmid obtained by inserting attL and attR genes which are the attachment sites of lambda phage, and a cat gene which is the antibiotic resistance gene to pMW118 (TaKaRa Bio). The genes are inserted in the order of attL-cat-attR. The attL sequence is shown in SEQ ID NO: 5 and the attR sequence is shown in SEQ ID NO: 6.

PCR was performed by using primers shown in SEQ ID NOS: 1 and 2, and having sequences corresponding to their 3' terminus ends of attL and attR and sequences corresponding to parts of the sfcA gene at their 5' terminus, respectively.

The amplified PCR product was purified on an agarose gel and introduced into *Escherichia coli* WC196 containing plasmid pKD46 showing temperature-sensitive replication, by eletroporation. pKD46 (Proc. Natl. Acad. Sci. USA, 2000, 97, 6640-6645) includes a 2,154 nt DNA fragment of lambda phage (GenBank/EMBL accession No. J02459, 31088-33241) containing genes (γ, β, and exo genes) encoding Red recombinase of the λ Red homologous recombination system under the control of the arabinose-inducible $P_{araB}$ promoter. pKD46 is necessary for integrating the PCR product into the chromosome of the strain WC196.

Competent cells for electroporation were prepared as follows. The *Escherichia coli* WC196 which was cultured overnight at 30° C. in LB medium containing 100 mg/l ampicillin, was diluted 100 times with 5 mL SOB medium (Sambrook, J. et al., "Molecular Cloning A Laboratory Manual, Second Edition", Cold Spring Harbor Laboratory Press (1989)) containing amplicillin (50 mg/l) and L-arabinose (1 mM). The diluted product was cultured at 30° C. under aeration until the $OD_{600}$ became about 0.6, and then concentrated 100 times. Cells were washed three times with 10% glycerol to prepare cells ready for electroporation. Electroporation was performed with 70 μl competent cells and about 100 ng of the PCR product. 1 ml SOC medium (Sambrook, J. et al., "Molecular Cloning A Laboratory Manual, Second Edition", Cold Spring Harbor Laboratory Press (1989)) was added to the cells subjected to electroporation. The cells were cultured at 37° C. for 2.5 hours, and then plate-cultured on L-agar medium containing 25 mg/l Cm (chloramphenicol) at 37° C. to select a Cm-resistant recombinant. Then, to lose the plasmid pKD46, cells were subcultured twice at 42° C. on Cm-containing L-agar medium. The obtained colonies are tested for ampicillin resistance. An ampicillin-sensitive strain without pKD46 is obtained.

The deletion of the sfcA gene of the mutant identified by the chloramphenicol resistance gene was confirmed by PCR. The resultant sfcA-deficient strain was designated as WC196ΔsfcA::att-cat.

To eliminate the att-cat gene which had been integrated into the sfcA gene, a helper plasmid pMW-intxis-ts (its preparation is described below) was used. pMW-intxis-ts harbors a gene encoding integrase (Int) (SEQ ID NO: 7) and a gene encoding excisionase (Xis) (SEQ ID NO: 9) of lambda phage and shows temperature-sensitive replication. By introduction of the pMW-intxis-ts, recombination occurs due to the recognition of attL (SEQ ID NO: 5) and attR (SEQ ID NO: 6) on the chromosome, and the antibiotic resistance gene between attL and attR is excised, resulting in a structure whereby only attL or attR sequence remains on chromosome.

Competent cells of the strain WC196ΔsfcA::att-cat were prepared according to an ordinary method, transformed with the helper plasmid pMW-intxis-ts, and plate-cultured at 30° C. on L-agar medium containing 50 mg/l ampicillin to select an ampicillin-resistant strain.

To lose the plasmid pMW-intxis-ts, cells were subcultured twice at 42° C. on L-agar medium. The obtained colonies are tested for ampicillin resistance and chloramphenicol resistance. An ampicillin- and chloramphenicol-sensitive strain without att-cat and pMW-intxis-ts is obtained. This strain was designated as WC196ΔsfcA.

(2) Disruption of b2463 Gene

Deletion of the b2463 gene in strains WC196 and WC196ΔsfcA was performed according to the method of (1) except primers of SEQ ID NOS: 3 and 4 were used as primers for disrupting b2463. Thus, the strains WC196Δb2463 and WC196ΔsfcAΔb2463 were obtained. The obtained strain WC196ΔsfcAΔb2463 was designated as WC196Δmez.

(3) Preparation of PCR Template and Helper Plasmid

The PCR template pMW118-attL-Cm-attR and the helper plasmid pMW-intxis-ts were prepared as follows:

(3-1) pMW118-attL-Cm-attR

For construction of the plasmid pMW118-attL-Cm-attR, the pMW118-attL-Tc-attR was used to start. Four DNA fragments were ligated:

1) BglII-EcoRI—the DNA fragment (120 bp) (SEQ ID NO: 5) carrying attL which was obtained by PCR amplification of the corresponding sequence of *E. coli* W3350 (contained λ prophage) chromosome using the oligonucleotides P1 and P2 (SEQ ID NOS: 11 and 12) as primers (these primers contained the subsidiary recognition sites for BglII and EcoRI endonucleases);

2) PstI-HindIII—the DNA fragment (182 bp) carrying attR (SEQ ID NO: 6) which was obtained by PCR amplification of the corresponding sequence of *E. coli* W3350 (contained λ prophage) chromosome using the oligonucleotides P3 and P4 (SEQ ID NOS: 13 and 14) as primers (these primers contained the subsidiary recognition sites for PstI and HindIII endonucleases);

3) the large (3916 bp) BglII-HindIII fragment of pMW118-ter_rrnB. pMW118-ter_rrnB was obtained by ligation of three DNA fragments:

the large (2359 bp) fragment carrying the AatII-EcoRI-pol fragment of the pMW118, pMW118 was digested with EcoRI restriction endonuclease, treated with Klenow fragment of DNA polymerase I and then was digested with AatII restriction endonuclease;

the small fragment (1194 bp) AatII-BglII of pUC19 carrying the bla gene for ampicillin resistance ($Ap^R$) was obtained by PCR amplification of the corresponding sequence of pUC19 plasmid using oligonucleotides P5 and P6 (SEQ ID NOS: 15 and 16) as primers (these primers contained the subsidiary recognition sites for AatII and BglII endonucleases);

the small fragment (363 bp) BglII-PstIpol of the transcription terminator ter_rrnB was obtained by PCR amplification of the corresponding region of *E. coli* MG1655 chromosome using the oligonucleotides P7 and P8 (SEQ ID NOS: 17 and 18) as primers (these primers contained the subsidiary recognition sites for BglII and PstI endonucleases);

4) the small fragment (1388 bp) EcoRI-PstI (SEQ ID NO: 23) of pML-Tc-ter_thrL including the gene for tetracycline resistance and the transcription terminator ter_thrL, the pML-Tc-ter_thrL was obtained in the following way:

the pML-MSC (2001 #5) was digested with XbaI and BamHI restriction endonucleases and then the large (3342 bp) fragment was ligated with the fragment (68 bp) XbaI-BamHI carrying terminator ter_thrL which was obtained by PCR amplification of the corresponding region of *E. coli* MG1655 chromosome using the oligonucleotides P9 and P10 (SEQ ID NOS: 19 and 20) as primers (these primers contained the subsidiary recognition sites for XbaI and BamHI endonucleases), the product of this reaction was the plasmid pML-ter_thrL;

then the pML-ter_thrL was digested with KpnI and XbaI restriction endonucleases then treated with Klenow fragment of DNA polymerase I and then was ligated with the small (1317 bp) EcoRI-Van91I fragment of pBR322 including the gene for tetracycline resistance (pBR322 was digested with EcoRI and Van91I restriction endonucleases then which have been treated with Klenow fragment of DNA polymerase I), the product of this reaction was the plasmid pML-Tc-ter_thrL;

so pMW118-attL-Tc-attR was obtained.

pMW118-attL-Cm-attR was constructed by ligation of large (4413 bp) BamHI-XbaI fragment of pMW118-attL-Tc-attR and BglII-XbaI the artificial DNA fragment (1162 bp) including the promoter $P_{A2}$ (the early promoter of the phage T7), the cat gene for chloramphenicol resistance ($Cm^R$), the transcription terminator ter_thrL and attR. The artificial DNA fragment (SEQ ID NO: 24) was obtained in the following way:

1. the pML-MSC (2001 #5) was digested with KpnI and XbaI restriction endonucleases and ligated with the small (120 bp) KpnI-XbaI fragment which includes the promoter $P_{A2}$ (the early promoter of the phage T7) obtained by PCR amplification of the corresponding region of phage T7 DNA the oligonucleotides P11 and P12 (SEQ ID NOS: 21 and 22) as primers (these primers contained the subsidiary recognition sites for KpnI and XbaI endonucleases), the product of this reaction was the plasmid pML-$P_{A2}$-MCS;
2. then the XbaI site was deleted from the pML-$P_{A2}$-MCS, the product of this reaction was the plasmid pML-$P_{A2}$-MCS (XbaI⁻);
3. then the small fragment (928 bp) BglII-HindIII of the pML-$P_{A2}$-MCS(XbaI⁻) including the promoter $P_{A2}$ (the early promoter of the phage T7) and gene cat for chloramphenicol resistance ($Cm^R$) was ligated with the small (234 bp) fragment HindIII-HindIII of pMW118-attL-Tc-attR including the transcription terminator ter_thrL and attR;
4. the required artificial DNA fragment (1156 bp) was obtained by PCR amplification with the ligation reaction mixture using the oligonucleotides P9 and P4 (SEQ ID NOS: 19 and 14) as primers (these primers contained the subsidiary recognition sites for HindIII and XbaI endonucleases).

(3-2) pMW-intxis-ts

Initially, two DNA fragments were amplified using phage λ DNA ("Fermentas") as a template. The first one included the region from nt 37168 to 38046 (SEQ ID NO: 33) and also contained the gene encoding the cI repressor, promoters Prm and Pr, and leader sequence of the cro gene. This fragment was obtained using the P1' and P2' oligonucleotides (SEQ ID NOS: 25 and 26) as primers. The second fragment carried xis-int genes of phage λ and comprised the region from nt 27801 to 29100 (SEQ ID NO: 34). Oligonucleotides P3' and P4' (SEQ ID NOS: 27 and 28) were used as primers for its amplification. All primers contained appropriate endonuclease recognition sites.

The obtained PCR-amplified fragment, carring the cI repressor, was digested with restriction endonuclease ClaI, treated with Klenow fragment of DNA polymerase I, and then digested with EcoRI restriction endonuclease. The second PCR-amplified fragment was digested with EcoRI and PstI restriction endonucleases. Then the pMWPlaclacI-ts plasmid was digested with BglII endonuclease, treated with Klenow fragment of DNA polymerase I and then digested with PstI restriction endonuclease. A vector fragment of pMWPlaclacI-ts was eluted from the agarose gel and ligated with the digested PCR-amplified fragments.

Plasmid pMWPlaclacI-ts is a derivative of pMWPlaclacI which consist of the following parts: 1) BglII-HindIII—artificial DNA fragment including the laci gene under control of the $P_{lacUV5}$ promoter and RBS of bacteriophage T7 gene 10; 2) AatII-BglII—DNA fragment carrying the gene for ampicillin resistance ($Ap^R$) which was obtained by PCR amplification of the corresponding sequence of pUC19 plasmid using oligonucleotides P5' and P6' (SEQ ID NOS: 29 and 30) as primers (these primers contained the subsidiary recognition sites for AatII and BglII endonucleases); 3) AatII-HindIII—fragment comprising AatII-PvuI fragment of the previously constructed recombinant plasmid—pMW118-ter_rrnB. The later plasmid was constructed in the following fashion: the PstI-HindIII DNA fragment carrying terminator ter_rrnB has been obtained by PCR amplification of the corresponding region of E. coli MG1655 chromosome using the oligonucleotides P7' and P8' (SEQ ID NOS: 31 and 32) containing appropriate endonuclease recognition sites as primers. Before ligation, pMW118 plasmid and ter_rrnB DNA fragment (complement, SEQ ID NO: 35) were restricted with PvuI or PstI endonuclease respectively, treated with Klenow fragment of DNA polymerase I to obtain the blunt ends and then restricted with AatII or HindIII endonuclease. To construct the pMWPlaclacI-ts variant the AatII-EcoRV fragment of the pMWPlaclacI plasmid was substituted by AatII-EcoRV fragment of the plasmid pMAN997 including the loci par, ori and $repA^{ts}$ gene of pSC101 replicon.

Example 4

Construction of Malic Enzyme-Deficient L-Threonine-Producing Bacterium sfcA- and b2463-deficient strains were constructed from strain VKPM B-5318. The strain VKPM B-5318 strain was deposited at Russian National Collection of Industrial Microorganisms (VKPM), GNII Genetika) on Nov. 19, 1987 and received an accession number of VKPM B-5318.

A strain which was deficient in one of the malic enzyme (mez) genes (sfcA, b2463) was obtained in the same way as in Example 3 using the "red-driven integration" method. Namely, it was performed in the same way using the "red-driven integration" method in Example 3 except that the strain B-5318 was used instead of the strain WC196 to obtain the sfcA- or b2463-deficient strain as a mutant identified by the chroramphenicol resistance gene. The strain B-5318 in which sfcA was disrupted was designated as B-5318ΔsfcA. The strain B-5318 in which b2463 was disrupted was designated as B-5318Δb2463. A strain B-5318 with disrupted sfcA and b2463 genes, B-5318ΔsfcAΔb2463 was obtained in the same way using "red-driven integration" and the excision system method as in Example 3. The strain B-5318ΔsfcAΔb2463 was designated as B-5318Δmez.

Example 5

Evaluation of Malic Enzyme-Deficient Strain

<5-1> Evaluation of L-Threonine-Producing Bacterium which is b2463-Deficient Strain The strains B-5318Δb2463 and B-5318 were each cultured on LB agar medium (10 g/L of trypton, 5 g/L of yeast extract, 5 g/L of NaCl and 15 g/L of agar) containing 20 mg/L of streptomycin sulfate and 25 mg/L of kanamycin sulfate at 37° C. for 24 hours, and bacterial cells were taked from one-fifth of the plate and inoculated into 50 mL of LB liquid medium (10 g/L of trypton, 5 g/L of yeast extract, and 5 g/L of NaCl) containing 20 mg/L of streptomycin sulfate and 25 mg/L of kanamycin sulfate to perform preculture at 40° C. and 144 rpm for 3.5 hours.

After the completion of the preculture, the preculture broth was inoculated into 300 mL of a main culture medium contained in a 1 L-volume jar fermenter in an amount of 10% of the volume of the main culture medium to perform the main culture at 40° C. and pH 7.0. The composition of the main culture medium is shown below.

TABLE 4

[Composition of main culture medium]

| | |
|---|---|
| Glucose | 100 g/L |
| Yeast extract | 1.8 g/L |
| FeSO$_4$·7H$_2$O | 18 mg/L |
| MnSO$_4$·4H$_2$O | 18 mg/L |
| KH$_2$PO$_4$ | 1.0 g/L |
| MgSO$_4$·7H$_2$O | 0.36 g/L |
| (NH$_4$)$_2$SO$_4$ | 4.5 g/L |
| NaCl | 0.6 g/L |
| Streptmycin sulfate | 20 mg/L |
| Kanamycin sulfate | 25 mg/L | pH during the culture was adjusted to 7.0 by adding ammonia gas.

After the added sugar was consumed, the amount of L-threonine was measured by liquid chromatography. The results are shown in Table 5.

When the b2463-deficient strain B-5318Δb2463 was used, the threonine yield was increased compared with the control strain B-5318.

TABLE 5

| Strain | Fermentation yield of L-threonine (%) |
|---|---|
| B-5318 | 31.4 |
| B-5318Δb2463 | 32.1 |

<5-2> Evaluation of L-Threonine-Producing Bacterium which is sfcA-Deficient Strain The strains B-5318ΔsfcA and B5318 were cultured in the same way as in <5-1>.

After the added sugar was consumed, the amount of L-threonine was measured by liquid chromatography. The results are shown in Table 6.

When the b2463-deficient strain B-5318ΔsfcA was used, the threonine yield was increased compared with the control strain B-5318.

TABLE 6

| Strain | Fermentation yield of L-threonine (%) |
|---|---|
| B-5318 | 31.4 |
| B-5318ΔsfcA | 32.2 |

<5-3> Evaluation of L-Lysine-Producing Bacterium which is sfcA- and b2463-Deficient Strain The strains WC196, WC196ΔsfcA and WC196Δb2463 were transformed according to an ordinary method using a plasmid for lysine production which harbored dapA, dapB and dapC genes, pCABD2 (International Publication No. WO 01/53459) to obtain strains WC196/pCABD2, WC196ΔsfcA/pCABD2 and WC196Δb2463/pCABD2.

The strains WC196/pCABD2, WC196ΔsfcA/pCABD2 and WC196Δb2463/pCABD2 were cultured at 37° C. with L medium (as described below) containing 20 mg/l streptomycin until OD$_{600}$ on the medium became about 0.6. Then, an amount equivalent to the culture, of 40% glycerol solution was added to the culture. After stirring, the mixture is dispensed in appropriate aliquots and stored at –80° C. The stored aliquots are called glycerol stocks.

The glycerol stocks of the strains were thawed, and each 100 μl was uniformly spread on an L plate containing 20 mg/l streptomycin and cultured at 37° C. for 24 hours. The bacterial cells were taken from one-eighth of the obtained plate and inoculated into 20 mL of a fermentation medium (as described below) containing 20 mg/L of streptomycin to culture at 37° C. for about 16 hours by a reciprocating shaker. After the culture, amounts of lysine which had accumulated in the medium and the remaining glucose were measured by Biotech Analyzer AS210 (Sakura Seiki).

The results of L-lysine accumulation and cell-subtracted yield are shown in Table 7. The cell-subtracted yield which is a yield calculated by subtracting the amount of sugar used for bacterial cell formation, is calculated based on an assumption that 50% of consumed sugar is used for bacterial cell formation. As seen from the results, the cell-subtracted yields of the strains WC196ΔsfcA/pCABD2 and WC196Δb2463/pCABD2 increase compared that of the control strain WC196/pCABD2.

TABLE 7

| Strain | | Dry cell | Cell-subtracted |
|---|---|---|---|
| Host | Plasmid | weight (g/L) | yield (%) |
| WC196 | pCABD2 | 2.5 | 100.0 |
| WC196ΔsfcA | pCABD2 | 2.3 | 101.6 |
| WC196Δb2463 | pCABD2 | 2.2 | 104.7 |

The mediums used for evaluation of the sfcA- or b2463-deficient L-lysine-producing strain are described below. The reagents used were obtained from Wako Pure Chemicals or Nakarai Tesque unless otherwise noted. The compositions of the media used are shown below. pH was adjusted with NaOH or HCl for all media.

TABLE 8

(L medium)

| | |
|---|---|
| Bacto trypton (DIFCO) | 10 g/L |
| Yeast extract (DIFCO) | 5 g/L |
| NaCl | 5 g/L |
| pH 7.0 | |

[steam-sterilized at 120° C. for 20 minutes]

(L agar medium)

| | |
|---|---|
| L medium | |
| Bacto agar (DIFCO) | 15 g/L |

[steam-sterilized at 120° C. for 20 minutes]

(L-Lysine production medium for *Escherichia* bacteria)

| | |
|---|---|
| Glucose | 40 g/L |
| Ammonium sulfate | 24 g/L |
| Potassium dihydrogen phosphate | 1.0 g/L |
| Magnesium sulfate heptahydrate | 1.0 g/L |
| Iron (II) sulfate heptahydrate | 0.01 g/L |
| Manganous sulfate tetrahydrate | 0.01 g/L |
| Yeast exatract | 2.0 g/L |
| Calcium carbonate (Pharmacopeia) | 30 g/L |

[adjusted to pH 7.0 with potassium hydroxide and steam-sterilized at 115° C. for 10 minutes provided that glucose and MgSO$_4$·7H$_2$O were separately sterilized.]

Example 6

Evaluation of Malic Enzyme-Deficient Strain (Δmez)

<6-1> Evaluation of L-Threonine-Producing Bacterium which is Malic Enzyme Deficient Strain The strains B-5318Δmez and B-5318 were each cultured on LB agar medium (10 g/L of trypton, 5 g/L of yeast extract, 5 g/L of NaCl and 15 g/L of agar) containing 20 mg/L of streptomycin sulfate and 25 mg/L of kanamycin sulfate at 37° C. for 24 hours, and bacterial cells were taken from one of the plates and suspended in 5 ml of LB liquid medium (10 g/L of trypton, 5 g/L of yeast extract, and 5 g/L of NaCl). 0.5 ml of the suspension was inoculated into 50 mL of LB liquid medium containing 20 mg/L of streptomycin sulfate and 25 mg/L of kanamycin sulfate to perform preculture at 39° C. and 144 rpm for 4 hours.

After the completion of the preculture, the preculture broth was inoculated into 300 mL of a main culture medium contained in a 1 L-volume jar fermenter in an amount of 10% of the volume of the main culture medium to perform the main culture at 39° C. and pH 7.0. The composition of the main culture medium is shown below.

TABLE 9

| [Composition of main culture medium] | |
|---|---|
| Glucose | 27 g/L |
| Yeast extract | 1.8 g/L |
| FeSO$_4$.7H$_2$O | 18 mg/L |
| MnSO$_4$.4H$_2$O | 18 mg/L |
| KH$_2$PO$_4$ | 1.5 g/L |
| MgSO$_4$.7H$_2$O | 0.36 g/L |
| (NH$_4$)$_2$SO$_4$ | 4.5 g/L |
| NaCl | 0.6 g/L |
| Streptmycin sulfate | 20 mg/L |
| Kanamycin sulfate | 25 mg/L | pH during the culture was adjusted to 7.0 by adding ammonia gas.

After the added sugar was consumed and exhausted, 600 g/l aqueous glucose solution was added.

After 24-hour main culture, the amount of L-threonine was measured by liquid chromatography. The results are shown in Table 10.

When the malic enzyme-deficient strain B-5318Δmez was used, the threonine yield was increased compared with the control strain B-5318.

TABLE 10

| Strain | Fermentation yield of L-threonine (%) |
|---|---|
| B-5318 | 35.9 |
| B-5318Δmez | 38.3 |

<6-2> Evaluation of L-Lysine-Producing Bacterium which is Malic Enzyme-Deficient Strain The strains WC196 and WC196Δmez were transformed according to an ordinary method with plasmid for lysine production, pCABD2 (International Publication No. WO 01/53459) to obtain strains WC196/pCABD2 and WC196Δmez/pCABD2.

The strains WC196/pCABD2 and WC196Δmez/pCABD2 were cultured at 37° C. with L medium (the same as used in Example 5 <5-3>) containing 20 mg/l streptomycin until OD$_{600}$ on the medium became about 0.6. Then, an amount equivalent to the culture, of 40% glycerol solution was added to the culture. After stirring, the mixture is dispensed in appropriate aliquots and stored at −80° C. The stored aliquots are called glycerol stocks.

The glycerol stocks of the strains were thawed, and each 100 μl was uniformly spread on an L plate containing 20 mg/l streptomycin and cultured at 37° C. for 24 hours. The bacterial cells were taken from one-eighth of the obtained plate and inoculated into 20 mL of a fermentation medium (the same as used in Example 5 <5-3>) containing 20 mg/L of streptomycin to culture at 37° C. for about 48 hours by a reciprocating shaker. After the culture, amounts of lysine which had accumulated in the medium and the remaining glucose were measured by Biotech Analyzer AS210 (Sakura Seiki).

The results of L-lysine accumulation and cell-subtracted yield are shown in Table 11. The cell-subtracted yield is calculated based on an assumption that 50% of consumed sugar is used for bacterial cell formation. As seen from the results, the cell-subtracted yield of the strain WC196Δmez/pCABD2 increases compared that of the control strain WC196/pCABD2.

TABLE 11

| Strain | | Dry cell | Cell-subtracted |
|---|---|---|---|
| Host | Plasmid | weight (g/L) | yield (%) |
| WC196 | pCABD2 | 5.2 | 100.0 |
| WC196Δmez | pCABD2 | 5.8 | 103.4 |

INDUSTRIAL APPLICABILITY

According to the present invention, metabolic fluxes affecting substance production can be efficiently determined, and thereby a guideline for improving a bacterial strain can be provided. Furthermore, a method for improving a bacterial strain based on this guideline can also be provided.

The invention claimed is:

1. A method for determining a metabolic flux that affects production of a desired substance, comprising the steps of:
   (A) creating a stoichiometric matrix based on formulas of biochemical reactions affecting production of said desired substance;
   (B) selecting a number of independent fluxes from all fluxes of said biochemical reactions, wherein the number of independent fluxes is the same as the degree of freedom of said stoichiometric matrix;
   (C) creating a number of flux distributions, wherein (i) each flux distribution is calculated from a random combination of said independent fluxes and (ii) said number is sufficient for a statistical analysis; and
   (D) obtaining a regression equation from said flux distributions, wherein said regression equation has a function that includes the minimum number of said independent fluxes for said function to show a correlation to the production of said desired substance, whereby a metabolic flux is determined that is comprised of said minimum number of independent fluxes and that affects the production of said desired substance,
wherein said steps are performed by a computer that is specially programmed therefor.

2. The method of claim 1, wherein said correlation of step D) has a correlation coefficient that is 0.8 or higher.

3. The method of claim 1, wherein said correlation of step D) has a correlation coefficient that is 0.9 or higher.

4. The method according to claim 1, wherein said regression equation is obtained by a multivariate linear regression analysis.

5. The method according to claim 1, wherein said method is performed for a microorganism having an ability to produce an amino acid, a nucleic acid or an organic acid.

6. A method for obtaining a bacterial strain capable of producing a desired substance, said method comprising:
   (A) determining a metabolic flux that affects production of said desired substance according to claim 1, wherein each of said independent fluxes has a correlation to the production of said desired substance, and
   (B) modifying a bacterial strain, such that activity of the independent fluxes positively correlated to the production of said desired substance is increased, or activity of the independent fluxes negatively correlated to the production of said desired substance is attenuated.

7. A method for producing a desired substance, comprising:
   (A) producing and accumulating said desired substance by cultivating the bacterial strain obtained according to claim 6, and
   (B) collecting the substance obtained in step (A), wherein said desired substance is an amino acid, a nucleic acid, or an organic acid.

* * * * *